US007256274B2

(12) United States Patent
Noteborn et al.

(10) Patent No.: US 7,256,274 B2
(45) Date of Patent: Aug. 14, 2007

(54) APOPTIN-ASSOCIATING PROTEIN

(75) Inventors: Mathieu Hubertus M. Noteborn, Leiderdorp (NL); Astrid Adriana A. M. Danen-van Oorschot, Berkel en Rodenrijs (NL); Jennifer Leigh Rohn, Amsterdam (NL); Bertram Weiss, Berlin (DE); Luisella Toschi, Berlin (DE)

(73) Assignee: Leadd B.V., Leiden (NL)

( * ) Notice: Subject to any disclaimer, the term of this patent is extended or adjusted under 35 U.S.C. 154(b) by 467 days.

(21) Appl. No.: 09/733,416

(22) Filed: Dec. 8, 2000

(65) Prior Publication Data

US 2003/0091996 A1 May 15, 2003

(51) Int. Cl.
*C07H 21/04* (2006.01)
(52) U.S. Cl. .................................... 536/23.1
(58) Field of Classification Search ............... 536/23.1
See application file for complete search history.

(56) References Cited

U.S. PATENT DOCUMENTS

| 5,981,205 | A | 11/1999 | Hemmings et al. |
| 6,809,189 | B2 | 10/2004 | Noteborn et al. |
| 6,878,692 | B2 | 4/2005 | Noteborn et al. |
| 2003/0105315 | A1 | 6/2003 | Specht et al. |

FOREIGN PATENT DOCUMENTS

| EP | 0921192 | | 6/1999 |
| EP | 0921192 | A1 | 6/1999 |
| EP | 0924296 | | 6/1999 |
| EP | 0924296 | A2 | 6/1999 |
| EP | 1 106 691 | A1 | 12/1999 |
| EP | 1 111 045 | A2 | 12/2000 |
| EP | 1 111 045 | A3 | 12/2000 |
| WO | WO 98/39448 | | 9/1998 |
| WO | WO 99/28460 | | 6/1999 |
| WO | WO 9928461 | | 6/1999 |
| WO | WO 01/42461 | A3 | 6/2001 |

OTHER PUBLICATIONS

Crystal, R.G. (Science, vol. 270, Oct. 1995, pp. 404-410).*
Tait et al. (Clin.Canc.Res., vol. 5, Jul. 1999, pp. 1708-1714).*
Gura (Science, v278, 1997, pp. 1041-1042).*
Reiger et al (Glossary of Genetics and Cytogenetics, Classical and Molecular, 4th Ed., Springer-Verlay, Berlin, 1976).*
Zachariae et al (Science Nov. 1996;274:1201-1204).*
Teodoro et al (Genes Dev. Aug. 15, 2004;18(16):1952-7).*
Overbeek (Transgenic Animal Technology 1994;p. 96-98).*
Wall (Theriogenology 1996; 45:57-68).*
Houdebine (J. Biotech 1994; 34:269-287).*
Kappell (Current Opin Biotech 1992;3:548-553).*
Cameron et al (Mol. Biol 1997;7:253-265).*
Niemann (Trans Res. 1997;7:73-75).*
Mullins (Hypertension 1993;22:630-633.*
Mullins (Nature 1990; 344:541-544.*
Hammer (Cell 1990; 63:1099-1112).*
Mullins (EMBO J. 1989;8:4065-4072).*
Taurog (J. Immunol 1988;141:4020-4023).*
Mullins (J. Clin. Invest. 1996; 98:S37-S40.*
Danen-Van Oorschot, A.A.A.M. et al., (1997). Apoptin induces apoptosis in human transformed and malignant cells but not in normal cells. Proceedings National Academy Sciences, USA: 94, 5843-5847.
Danen-Van Oorschot, A.A.A.M. et al., (1997). BAG-1 inhibits p53-induced but not Apoptin-induced apoptosis. Apoptosis: 2, 395-402.
Noteborn et al., (1994). A single chicken anemia virus protein induces apoptosis. Journal of Virology: 68, 346-351.
Noteborn et al., (1998). Chicken anemia virus: Induction of apoptosis by a single protein of a single stranded DNA virus. Seminars in Virology: 8, 497-504.
Pietersen, A. M. et al., (1999). Specific tumor-cell killing with adenovirus vectors containing the Apoptin gene. Gene Therapy: 6, 882-892.
Thompson, C. B. (1995). Apoptosis in the pathogenesis and treatment of disease. Science: 267, 1456-1462.
Zhuang, S. -M. et al., (1995). Apoptin, a protein encoded by chicken anemia virus, induces cell death in various human hematologic malignant cells in vitro. Leukemia: 9, S1, 118-120.
Zhuang, S. -M. et al., (1995). Apoptin, a protein derived from chicken anemia virus, induces a p53-independent apoptosis in human osteosarcoma cells. Cancer Research: 55, No. 3, 486-489.
T. Jenuwein et al., (1998). Cell. Mol. Life Sci.: 54, 80-93.
T. Rozovskaia et al., (2000). Oncogene: 19, 351-357.
S. Jacobson et al., (1999). Curr. Opinion in Gen. & Dev.: 9, 175-184.
Lai C -H. et al., (2000). "Identification of novel human genes evolutionarily conserved in Cernorhabditis elegans." Genome Res., vol. 10, No. 5, pp. 703-713.
Lai C. -H., "*Homo sapiens* CG1-85 protein." EMBL Sequences Accession No. AF151843, Jun. 6, 1999.
Zhuang et al., Apoptin, a Protein Derived from Chicken Anemia Virus, Induces p53-independent Apoptosis in Human Osteosarcoma Cells, Cancer Res, Feb. 1995, pp. 486-489, vol. 55, No. 3.
Pietersen et al., Specific tumor-cell killing with adenovirus vectors containing the apoptin gene, Gene Therapy, 1999, pp. 882-892, vol. 6.
Bellamy, Christopher O.C., et al., "Cell death in health and disease: the biology and regulation of apoptosis," Seminars in Cancer Biology, vol. 6, pp. 3-16 (1995).
Danen-Van Oorschot, A.A.A.M., et al., "Apoptin induces apoptosis in human transformed and malignant cells but not in normal cells." Proc. Natl. Acad Sci. USA vol. 94, pp. 5843-5847 (May 1997).
Danen-van Oorschot, et al., A.A.A.M., "BAG-1 inhibits p53-induced but not apoptin-induced apoptosis," Apoptosis, vol. 2, No. 4, pp. 395-402 (1997).

(Continued)

*Primary Examiner*—Christopher H. Yaen
(74) *Attorney, Agent, or Firm*—TraskBritt

(57) ABSTRACT

The invention relates to the field of apoptosis. The invention provides novel therapeutic possibilities, for example novel combinatorial therapies or novel therapeutic compounds that can work alone, sequentially to, or jointly with Apoptin, especially in those cases wherein p53 is (partly) nonfunctional.

12 Claims, 10 Drawing Sheets

OTHER PUBLICATIONS

Duke, Richard C., et al, "Cell Suicide in Health and Disease," Scientific American, pp. 80-87 (Dec. 1996).

Noteborn, M.H.M., et al., "A Single Chicken Anemia Virus Protein Induces Apoptosis," Journal of Virology, vol. 68, No. 1, pp. 346-351 (Jan. 1994).

Noteborn, M.H.M., et al., "Characterization of Cloned Chicken Anemia Virus DNA That Contains All Elements for the Infectious Replication Cycle." Journal of Virology, vol. 65, No. 6, pp. 3131-3139 (Jun. 1991).

Noteborn, Mathieu H.M., et al, "Chicken Anemia Virus Induction of Apoptosis by a Single Protein of a Single-Stranded DNA Virus," Seminars in Virology, vol. 8, pp. 497-504 (1998).

Noteborn, Mathieu H.M., et al., "Simultaneous expression of recombinant baculovirus-encoded chicken anaemia virus (CAV) proteins VP1 and VP2 is required for formation of the CAV-specific neutralizing epitope," Journal of General Virology, vol. 79, pp. 3073-3077 (1998).

Paulovich, Amanda G., et al., "When Checkpoints Fail," Cell, vol. 88, pp. 315-321 (Feb. 7, 1997).

Steller Hermann, "Mechanisms and Genes of Cellular Suicide," Science, vol. 267, pp. 1445-1449 (Mar. 10, 1995).

Teodoro, Jose G, et al., "Regulation of Apoptosis by Viral Gene Products," Journal of Virology, vol. 71, No. 3, pp. 1739-1746 (Mar. 1997).

Thompson, Craig B, "Apoptosis in the Pathogenesis and Treatment of Disease," Science, vol. 267, pp. 1456-1462 (Mar. 10, 1995).

Strausberg, Robert, "qy85c09.x1 NCI_CGAP_Bm25 *Homo sapiens* cDNA clone Image:2018800 3', mRNA sequence," Jan. 7, 1999, Accession No. A1360308.

Zhao S., "Use of BAC End Sequences from Library RPC1-11 for Sequence-Ready Map building," Mar. 15, 1999, Accession No. AQ382839.

Strausberg, Robert, "wd70d04.x1 NCI_CGAP_Lu24 *Homo sapiens* cDNA clone IMAGE:2336935 3', mRNA sequence," Jun. 3, 1999, Accession No. A1692778.

Benet et al., pp. 3-32, in The Pharmacological Basis of Therapeutics, 8th ed., McGraw-Hill, Inc., New York, 1990.

Jain et al., Vascular and interstitial barriers to delivery of therapeutic agents in tumors, Cancer and Metastasis Reviews, 1990, pp. 253-266, vol. 9.

Jain R.K, Delivery of Molecular Medicine to Solid Tumors, 1996, Science, pp. 1079-1080, vol. 271.

Dermer, Another Anniversary for the War on Cancer, Biotechnology, 1994, pp. 320, vol. 12.

Database GenEmbl on GenCore version 4.5, Accession No. AX015052, Oct. 1999.

Strausberg R. Database EST on GenCore version 4.5, Accession No. BE746443, Sep. 2000.

Danen-Van Oorschot et al., BCL-2 Stimulated Apoptin-induced Apoptosis, pp. 245-249 in Drug Resistance in Leukemia and Lymphoma III, ed. Kaspers et al., Kluwer Academic/Plenum Publishers, New York, 1999.

Noteborn et al., Apoptin-induced apoptosis: potential for antitumor therapy. Drug Resistance Updated, 1998. pp. 99-103, vol. 1.

Noteborn et al., Apoptin induces apoptosis in transformed cells specifically: Potentials for an antitumor therapy, Biogenic Amines, 1998, pp. 73-91, vol. 15, No. 1.

Abstract XP-002140967, May 1999.

Abstract XP-002140968, May 1995.

Abstract XP-002140969, 2000.

McDonnell et al., "Implications of apoptotic cell death regulation in cancer therapy," Cancer Biology, 1995, pp. 53-60, vol. 6.

Mullersman et al., "The PHD finger: implications for chromatin-mediated transcriptional regulation," TIBS 20, Feb. 1995, pp. 56-59.

Jacobson et al., "Modifying chromatin and concepts of cancer," Chromosomes and expression mechanisms, pp. 175-184.

Lu et al., "A Novel Gene (PLU-1) Containing Highly Conserved Putative DNA/Chromatin Binding Motifs Is Specifically Up-regulated in Breast Cancer," The Journal of Biological Chemistry, 1999, pp. 15633-15645, vol. 274, No. 22.

Zhuang et al., "Apoptin, a Protein Encoded by Chicken Anemia Virus, Induces Cell Death in Various Human Hematologic Malignant Cells in vitro," Leukemia, vol. 9, Suppl. 1, pp. S118-S120, 1995.

Strausberg, Robert, qt26b07.x1 Soares_pregnant_uterus_NbHPU Homo sapiens cDNA clone EMBL Database; Accession No. A1342119, Mar. 31, 1998, XP002140933.

\* cited by examiner start AAP4 cDNA

```
  1  GCCACGAAGG CCGGGAGAGC TCGCCCTGCA CCTACATAAC TCGGCGGTCA GTGAGGACAA
       adaptor
 61  GAACAAATCT GAAGGAGGCC TCTGACATCA AGCTTGAACC AAATACGTTG AATGGCTATA
121  AAAGCAGTGT GACGGAACCT TGCCCCGACA GTGGTGAACA GCTGCAGCCA GCTCCTGTGC
181  TGCAGGAGGA AGAACTGGCT CATGAGACTG CACAAAAAGG GGAGGCAAAG TGTCATAAGA
241  GTGACACAGG CATGTCCAAA AAGAAGTCAC GACAAGGAAA ACTTGTGAAA CAGTTTGCAA
301  AAATAGAGGA ATCTACTCCA GTGCACGATT CTCCTGGAAA AGACGACGCG GTACCAGATT
361  TGATGGGTCC CCATTCTGAC CAGGGTGAGC ACAGTGGCAC TGTGGGCGTG CCTGTGAGCT
421  ACACAGACTG TGCTCCTTCA CCCGTCGGTT GTTCAGTTGT GACATCAGAT AGCTTCAAAA
481  CAAAAGACAG CTTTAGAACT GCAAAAAAGT AAAAGAAGA GGCGAATCAC AAGGTATGAT
541  GCACAGTTAA TCCTAGAAAA TAACTCTGGG AGTCCCAAAT TGACTCTTCG TAGGCGTCAT
601  GATAGCAGCA GCAAACAAA TGGACCAAGA GAATGATGGG AATGAAACTC TTCCCAAAAT
661  TAAGCATCAA GTTAAGCCA AAGACCATGA CAACGATAAC AATCTCGATG TAGCAAAGTT
721  ATAAGGGTTT AGCTCAGGAT TAGGAATGTT TCACAAAATT AAAAAGGCAT
```

FIGURE 1

1    HEGRESSPCT YITRRSVRTR TNLKEASDIK LEPNTLNGYK SSVTEPCPDS GEQLQPAPVL

61   QEEELAHETA QKGEAKCHKS DTGMSKKKSR QGKLVKQFAK IEESTPVHDS PGKDDAVPDL

121  MGPHSDQGEH SGTVGVPVSY TDCAPSPVGC SVVTSDSFKT KDSFRTAKK* KEEANHKV*C

181  TVNPRK*LWE SQIDSS*AS* *QQQNKWTKR MMGMKLFPKL SIKFKPKTMT TITISM*QSY

241  KGLAQD*ECF TKLKRH

AAP-4 and/or Apoptin induce apoptosis in human tumor cells

Apoptosis activity in Saos-2 and U2OS cells

|  | LacZ | Synthesised proteins | | AAP-4/Apoptin |
|---|---|---|---|---|
|  |  | AAP-4 | Apoptin |  |
| Exp.1 (Saos-2) | - | ++ | ++ | +++ |
| Exp.2 (Saos-2) | - | ++ | ++ | +++ |
| Exp.3 (Saos-2) | - | ++ | ++ | +++ |
| Exp.1 (U2OS) | - | ++ | ++ | ND |
| Exp.2 (U2OS) | - | ++ | ++ | ND |
| Exp.3 (U2OS) | - | ++ | ++ | ND |

ND not determined

*: "circular" structures containing AAP-4 and apoptin

Figure 5

```
   1  CGGCAGGGCA GCGGGGCGAT GAGGTGAGGA CGCCCGGGAA CCGGAGGCGG
  51  CACCGCGCGG CGCACGGACC TGGACGCGG AGTCCTGAAG CCGGCGGACG
 101  GTTTTCGTAC GGGCGGCCGT GCGCGAGGCG AGGAGAGAAC ATTGAAAGTA
 151  TTCTCTAAGC TATTTGAAGA GAGTGACTAA ATGCACCTGG GTCAGGCTGT
 201  CTGTGGGTAT GAAGTGGTTG GGAGAATCCA AGAACATGGT GGTGAATGGC
 251  AGGAGAAATG GAGGCAAGTT GTCTAATGAC CATCAGCAGA ATCAATCAAA
 301  ATTACAGCAC ACGGGAAGG ACACCCTGAA GGCTGGCAAA AATGCAGTCG
 351  AGAGGAGGTC GAACAGATGT AATGGTAACT CGGGATTTGA AGGACAGAGT
 401  CGCTATGTAC CATCCTCTGG AATGTCCGCC AAGGAACTCT GTGAAAATGA
 451  TGACCTAGCA ACCAGTTTGG TTCTTGATCC CTATTTAGGT TTCAAACAC
 501  ACAAAATGAA TACTAGCGCC TTTCCTTCGA GGAGCTCAAG GCATTTTTCA
 551  AAATCTGACA GTTTTTCTCA CAACAACCCT GTGAGATTTA GGCCTATTAA
 601  AGGAAGGCAG GAAGAACTAA AGGAAGTAAT TGAACGTTTT AAGAAAGATG
 651  AACACTTGGA GAAAGCCTTC AAATGTTTGA CTTCAGGCGA ATGGGCACGG
 701  CACTATTTTC TCAACAAGAA TAAAATGCAG GAGAAATTAT TCAAAGAACA
 751  TGTATTTATT TATTTGCGAA TGTTTGCAAC TGACAGTGGA TTTGAAATAT
 801  TGCCATGTAA TAGATACTCA TCAGAACAAA ATGGAGCCAA AATAGTTGCA
 851  ACAAAAGAGT GGAAACGAAA TGACAAAATA GAATTACTGG TGGGTTGTAT
 901  TGCCGAACTT TCAGAAATTG AGGAGAACAT GCTACTTAGA CATGGAGAAA
 951  ACGACTTCAG TGTCATGTAC TCCACAAGGA AAAACTGTGC TCAACTCTGG
1001  CTGGGTCCTG CTGCGTTTAT AAACCATGAT TGCAGACCTA ATTGTAAGTT
1051  TGTGTCAACT GGTCGAGATA CAGCATGTGT GAAGGCTCTA AGAGACATTG
1101  AACCTGGAGA AGAAATTTCT TGTTATTATG GAGATGGGTT CTTTGGAGAA
1151  AATAATGAGT TCTGCGAGTG TTACACTTGC GAAAGACGGG GCACTGGTGC
1201  TTTTAAATCC AGAGTGGGAC TGCCTGCGCC TGCTCCTGTT ATCAATAGCA
1251  AATATGGACT CAGAGAAACA GATAAACGTT TAAATAGGCT TAAAAAGTTA
1301  GGTGACAGCA GCAAAAATTC AGACAGTCAA TCTGTCAGCT CTAACACTGA
1351  TGCAGATACC ACTCAGGAAA AAACAATGC AACTTCTAAC CGAAAATCTT
1401  CAGTTGGCGT AAAAAAGAAT AGCAAGAGCA GAACGTTAAC GAGGCAATCT
```

Fig. 5A

```
1451  ATGTCAAGAA TTCCAGCTTC TTCCAACTCT ACCTCATCTA AGCTAACTCA
1501  TATAAATAAT TCCAGGGTAC CAAAGAAACT GAAGAAGCCT GCAAAGCCTT
1551  TACTTTCAAA GATAAAATTG AGAAATCATT GCAAGCGGCT GGAGCAAAAG
1601  AATGCTTCAA GAAAACTCGA AATGGGAAAC TTAGTACTGA AAGAGCCTAA
1651  AGTAGTTCTG TATAAAAATT TGCCCATTAA AAAAGATAAG GAGCCAGAGG
1701  GACCAGCCCA AGCCGCAGTT GCCAGCGGGT GCTTGACTAG ACACGCGGCG
1751  AGAGAACACA GACAGAATCC TGTGAGAGGT GCTCATTCGC AGGGGGAGAG
1801  CTCGCCCTGC ACCTACATAA CTCGGCGGTC AGTGAGGACA AGAACAAATC
1851  TGAAGGAGGC CTCTGACATC AAGCTTGAAC CAAATACGTT GAATGGCTAT
1901  AAAAGCAGTG TGACGGAACC TTGCCCCGAC AGTGGTGAAC AGCTGCAGCC
1951  AGCTCCTGTG CTGCAGGAGG AAGAACTGGC TCATGAGACT GCACAAAAAG
2001  GGGAGGCAAA GTGTCATAAG AGTGACACAG GCATGTCCAA AAAGAAGTCA
2051  CGACAAGGAA AACTTGTGAA ACAGTTTGCA AAAATAGAGG AATCTACTCC
2101  AGTGCACGAT TCTCCTGGAA AAGACGACGC GGTACCAGAT TTGATGGGTC
2151  CCCATTCTGA CCAGGGTGAG CACAGTGGCA CTGTGGGCGT GCCTGTGAGC
2201  TACACAGACT GTGCTCCTTC ACCCGTCGGT TGTTCAGTTG TGACATCAGA
2251  TAGCTTCAAA ACAAAAGACA GCTTTAGAAC TGCAAAAAGT AAAAAGAAGA
2301  GGCGAATCAC AAGGTATGAT GCACAGTTAA TCCTAGAAAA TAACTCTGGG
2351  ATTCCCAAAT TGACTCTTCG TAGGCGTCAT GATAGCAGCA GCAAAACAAA
2401  TGACCAAGAG AATGATGGAA TGAACTCTTC CAAAATAAGC ATCAAGTTAA
2451  GCAAAGACCA TGACAACGAT AACAATCTCT ATGTAGCAAA GCTTAATAAT
2501  GGATTTAACT CAGGATCAGG CAGTAGTTCT ACAAAATTAA AAATCCAGCT
2551  AAAACGAGAT GAGGAAAATA GGGGGTCTTA TACAGAGGGG CTTCATGAAA
2601  ATGGGGTGTG CTGCAGTGAT CCTCTTTCTC TCTTGGAGTC TCGAATGGAG
2651  GTGGATGACT ATAGTCAGTA TGAGGAAGAA AGTACAGATG ATTCCTCCTC
2701  TTCTGAGGGC GATGAAGAGG AGGATGACTA TGATGATGAC TTTGAAGACG
2751  ATTTTATTCC TCTTCCTCCA GCTAAGCGCT TGAGGTTAAT AGTTGGAAAA
2801  GACTCTATAG ATATTGACAT TTCTTCAAGG AGAAGAGAAG ATCAGTCTTT
2851  AAGGCTTAAT GCCTAAGCTC TTGGTCTTAA CTTGACCTGG GATAACTACT
```

Fig. 5B

```
2901  TTAAAGAAAT AAAAAATTCC AGTCAATTAT TCCTCAACTG AAAGTTTAGT
2951  GGCAGCACTT CTATTGTCCC TTCACTTATC AGCATACTAT TGTAGAAAGT
3001  GTACAGCATA CTGACTCAAT TCTTAAGTCT GATTTGTGCA AATTTTTATC
3051  GTACTTTTTA AATAGCCTTC TTACGTGCAA TTCTGAGTTA GAGGTAAAGC
3101  CCTGTTGTAA AATAAAGGCT CAAGCAAAAT TGTACAGTGA TAGCAACTTT
3151  CCACACAGGA CGTTGAAAAC AGTAATGTGG CTACACAGTT TTTTTAACTG
3201  TAAGAGCATC AGCTGGCTCT TTAATATATG ACTAAACAAT AATTTAAAAC
3251  AAATCATAGT AGCAGCATAT TAAGGGTTTC TAGTATGCTA ATATCACCAG
3301  CAATGATCTT TGGCTTTTTG ATTTATTTGC TAGATGTTTC CCCCTTGGAG
3351  TTTTGTCAGT TTCACACTGT TTGCTGGCCC AGGTGTACTG TTTGTGGCCT
3401  TTGTTAATAT CGCAAACCAT TGGTTGGGAG TCAGATTGGT TTCTTAAAAA
3451  AAAAAAAAAA ATGACATACG TGACAGCTCA CTTTTCAGTT CATTATATGT

3501  ACGAGGGTAG CAGTGTGTGG GATGAGGTTC GATACAGCGT ATTTATTGCT
3551  TGTCATGTAA ATTAAAAACC TTGTATTTAA CTCTTTTCAA TCCTTTTAGA
3601  TAAAATTGTT CTTTGCAAGA ATGATTGGTG CTTATTTTTT CAAAAATTTG
3651  CTGTGAACAA CGTGATGACA ACAAGCAACA TTTATCTAAT GAACTACAGC
3701  TATCTTAATT TGGTTCTTCA AGTTTTCTGT TGCACTTGTA AAATGCTACA
3751  AGGAATATTA AAAAAATCTA TTCACTTTAA CTTATAATAG TTTATGAAAT
3801  AAAAACATGA GTCACAGCTT TTGTTCTGTG GTAACCTATA AAAAAAGTTT
3851  GTCTTTGAGA TTCAATGTAA AGAACTGAAA ACAATGTATA TGTTGTAAAT
3901  ATTTGTGTGT TGTGAGACAT TTTTGTCATA AGAAATTAAA AGAACTTACC
3951  AGGAAGGTTT TTAAGTTTAG AAATATTCAT GCCAATAAAA TAGGAAATTA
4001  TAAATATATA GTTTAAGCA CTGCATCAGT GGGAGTTCTT GGCTTATGTT
4051  AGTTTATGTT AGTTTATTAT GAAAACATCA AAGATTTTTT TGACTATATT
4101  ATCAGTTAAA CAAAAAGGAG TCAGATTTAA TTTGTTTTTT GAAGCACTTT
4151  GAGAAATTAA TTTTAATTAA CTTAATGAGC AAATTTTTAT TACTACTTTA
4201  TGTTCAATAC CAGGTTCTTT TCATTTCTCT GGATTATTTT GCAAATCATT
4251  GGACAGAGAA TTTGGGAATA TAAATCTGTA ACAGGTGTTG ACACCAGTAG
4301  GTCTCTTTAT TTCTGGGAAA TGTGTACCTG TACTTTCTGA TATACAGTGT
```

Fig 5C

```
4351  TCCTAAGTAA AAATCAATTC AGGGGATTTG TATAGTGTCT ATAGGAAAGT
4401  AGCCCATGTC TTGAAATATG AAAAGGAATC TGAAGGTCAT GAAAAGTCCA
4451  GTGGAGAAAA TCTCAATGCT TACTGTTACT ACTAATTGAT TCCTACTAGT
4501  TTCCAGGTTT GGGGGGATAT TGTTTCAATG ACGCTCCTTA AGACTGTTGA
4551  TTGCCCATAG GTTCCAAATA GAAATTAAGA CTCATGAACA TTTTTAGAAA
4601  GTAGATTGTT TTCTCCTGGT TCTCTAAGGA ACTACTTCTG CAGTCTTACA
4651  TAGTCTCATC CTTGTTTGTT GTGGTGCAGT CGAACTCCTC AGGCGTTTGG
4701  AAAGCATGTG GTAGACCTTC TTCCACACCC ACCCATACCC CCGTTCACTG
4751  CGTCTGGAGG TCTTCAACAG TGAAGTAGGG CAGCCCACAC AGCCTCTCAG
4801  GAGCACCTGT CCGAGGCACC CGGAGCACTT TGCAGAGCAC GTCCAGCCCT
4851  CATGGGGTCC CTGCATAGAA ATGTGAACCC CTGCCACTGA GGAAGATGAA
4901  GGTAGACCCT GTGTCTGGAG GTGCTGGAGG GCAGCGGGTC ACCTCTTGTA
4951  TTCCCACCTT AGTTTGGGGT GTTTTGAAGA GGTTCAGAGA CTAAATCTTA
5001  AACCTTATTT GAATACCAAC GATAGCTATT TTGGGAATTT CGATCTTAAA
5051  AAGTGACAAA ACACATTTCC CATTTTCATT TTTCAGCTGA ATTTTAGTAA
5101  CTTATTTTTG ATGTTTTAAT TTTATCATGG CCTCCTCTTT GGAGGCCAAC
5151  CTTCCCATGG GTCTCAAAGC AGTGACATTT GGTAGTAAAT CACTGCCTCT
5201  CAGGAGTCGG TATGCACAAG CACTCAGCAG CCACTGTTGA TGCCTTCTAG
5251  GGAAACCTAA TTTCCGTTGG TAAAGGTAGG GGCCTCGGAA CTGTTCCGGA
5301  TCTGCTGTAG AACTTCACCG TGTGGAATGG TGACAGCCAC ACACCGTTGA
5351  CCAGTTTAGA AGAGGTTGCA TTCAATAAAA CTCTTAGCTT GAGCTTATGC
5401  AATGATTGGT TAAGATTTTG GCATTGTAAG AATTAGGAGA TGATCATAGA
5451  AATATATGTA AAGTATTCAA TTTTCAATCA TTTTCAAATT ACTGTTATAA
5501  ATTGTTTTTG CTGAGTTGTA ATACTTTTGA GATACAATGT ATTCCTTGTA
5551  CTGAAAGAAT GAAAAAGGAC TTTTTCAGCA TTTGAGGTAA GTTCTTTAAC
5601  GTTTCATTAA AAACATTTTT TACAAATATT TTGTACATGC ACTTGCAGTA
5651  TTGAGGTTAA TCATTTTAAT AAATTCGGAA ATTAAAAAAA
```

```
  1  MVVNGRRNGG KLSNDHQQNQ SKLQHTGKDT LKAGKNAVER RSNRCNGNSG
 51  FEGQSRYVPS SGMSAKELCE NDDLATSLVL DPYLGFQTHK MNTSAFPSRS
101  SRHFSKSDSF SHNNPVRFRP IKGRQEELKE VIERFKKDEH LEKAFKCLTS
151  GEWARHYFLN KNKMQEKLFK EHVFIYLRMF ATDSGFEILP CNRYSSEQNG
201  AKIVATKEWK RNDKIELLVG CIAELSEIEE NMLLRHGEND FSVMYSTRKN
251  CAQLWLGPAA FINHDCRPNC KFVSTGRDTA CVKALRDIEP GEEISCYYGD
301  GFFGENNEFC ECYTCERRGT GAFKSRVGLP APAPVINSKY GLRETDKRLN
351  RLKKLGDSSK NSDSQSVSSN TDADTTQEKN NATSNRKSSV GVKKNSKSRT
401  LTRQSMSRIP ASSNSTSSKL THINNSRVPK KLKKPAKPLL SKIKLRNHCK
451  RLEQKNASRK LEMGNLVLKE PKVVLYKNLP IKKDKEPEGP AQAAVASGCL
501  TRHAAREHRQ NPVRGAHSQG ESSPCTYITR RSVRTRTNLK EASDIKLEPN
551  TLNGYKSSVT EPCPDSGEQL QPAPVLQEEE LAHETAQKGE AKCHKSDTGM
601  SKKKSRQGKL VKQFAKIEES TPVHDSPGKD DAVPDLMGPH SDQGEHSGTV
651  GVPVSYTDCA PSPVGCSVVT SDSFKTKDSF RTAKSKKKRR ITRYDAQLIL
701  ENNSGIPKLT LRRRHDSSSK TNDQENDGMN SSKISIKLSK DHDNDNNLYV
751  AKLNNGFNSG SGSSSTKLKI QLKRDEENRG SYTEGLHENG VCCSDPLSLL
801  ESRMEVDDYS QYEEESTDDS SSSEGDSEED DYDDDFEDDF IPLPPAKRLR
851  LIVGKDSIDI DISSRRREDQ SLRLNA*
```

Figure 7

```
185                                                   GFEILP CNRYSSEQNG

201  AKIVATKEWK RNDKIELLVG CIAELSEIEE NMLLRHGEND FSVMYSTRKN

251  CAQLWLGPAA FINHDCRPNC KFVSTGRDTA CVKALRDIEP GEEISCYYGD

301  GFFG
```

APOPTIN-ASSOCIATING PROTEIN

TECHNICAL FIELD

The invention relates to the field of apoptosis.

BACKGROUND

Apoptosis is an active and programmed physiological process for eliminating superfluous, altered or malignant cells (Earnshaw, 1995, Duke et al., 1996). Apoptosis is characterized by shrinkage of cells, segmentation of the nucleus, condensation and cleavage of DNA into domain-sized fragments, in most cells followed by internucleosomal degradation. The apoptotic cells fragment into membrane-enclosed apoptotic bodies. Finally, neighbouring cells and/or macrophages will rapidly phagocytose these dying cells (Wyllie et al., 1980, White, 1996). Cells grown under tissue-culture conditions and cells from tissue material can be analysed for being apoptotic with agents staining DNA, as e.g. DAPI, which stains normal DNA strongly and regularly, whereas apoptotic DNA is stained weakly and/or irregularly (Noteborn et al., 1994, Telford et al., 1992).

The apoptotic process can be initiated by a variety of regulatory stimuli (Wyllie, 1995, White 1996, Levine, 1997). Changes in the cell survival rate play an important role in human pathogenesis of diseases, e.g. in cancer development and auto-immune diseases, where enhanced proliferation or decreased cell death (Kerr et al., 1994, Paulovich, 1997) is observed. A variety of chemotherapeutic compounds and radiation have been demonstrated to induce apoptosis in tumor cells, in many instances via wild-type p53 protein (Thompson, 1995, Bellamy et al., 1995, Steller, 1995, McDonell et al., 1995).

Many tumors, however, acquire a mutation in p53 during their development, often correlating with poor response to cancer therapy. Certain transforming genes of tumorigenic DNA viruses can inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 1994, Sachs and Lotem, 1997).

For such tumors lacking functional p53 (representing more than half of the tumors) alternative anti-tumor therapies are under development based on induction of apoptosis independent of p53 (Thompson 1995, Paulovich et al., 1997). One has to search for the factors involved in induction of apoptosis, which do not need p53 and/or can not be blocked by anti-apoptotic activities, such as Bcl-2 or Bcr-abl-like ones. These factors might be part of a distinct apoptosis pathway or might be (far) downstream of the apoptosis inhibiting compounds.

Apoptin is a small protein derived from chicken anemia virus (CAV; Noteborn and De Boer, 1995, Noteborn et al., 1991, Noteborn et al., 1994; 1998a), which can induce apoptosis in human malignant and transformed cell lines, but not in untransformed human cell cultures. In vitro, Apoptin fails to induce programmed cell death in normal lymphoid, dermal, epidermal, endothelial and smooth-muscle cells. However, when normal cells are transformed they become susceptible to apoptosis by Apoptin. Long-term expression of Apoptin in normal human fibroblasts revealed that Apoptin has no toxic or transforming activity in these cells (Danen-van Oorschot, 1997 and Noteborn, 1996).

In normal cells, Apoptin was found predominantly in the cytoplasm, whereas in transformed or malignant cells i.e. characterized by hyperplasia, metaplasia ordysplasia, it was located in the nucleus, suggesting that the localization of Apoptin is related to its activity (Danen-van Oorschot et al. 1997). Apoptin-induced apoptosis occurs in the absence of functional p53 (Zhuang et al., 1995a), and cannot be blocked by Bcl-2, Bcr-abl (Zhuang et al., 1995), or the Bcl-2-associating protein BAG-1 (Danen-Van Oorschot, 1997a, Noteborn, 1996).

Therefore, Apoptin is a therapeutic compound for the selective destruction of tumor cells, or other hyperplasia, metaplasia or dysplasia, especially for those tumor cells which have become resistant to (chemo)-therapeutic induction of apoptosis, due to the lack of functional p53 and (over)-expression of Bcl-2 and other apoptosis-inhibiting agents (Noteborn and Pietersen, 1998). It appears, that even pre-malignant, minimally transformed cells, are sensitive to the death-inducing effect of Apoptin. In addition, Noteborn and Zhang (1998) have shown that Apoptin-induced apoptosis can be used as diagnosis of cancer-prone cells and treatment of cancer-prone cells.

The fact that Apoptin does not induce apoptosis in normal human cells, at least not in vitro, shows that a toxic effect of Apoptin treatment in vivo will be very low. Noteborn and Pietersen (1998) and Pietersen et al. (1999) have provided evidence that adenovirus expressed Apoptin does not have an acute toxic effect in vivo. In addition, in nude mice it was shown that Apoptin has a strong anti-tumor activity.

However, to further enlarge the array of therapeutic anti-cancer or anti-auto-immune-disease compounds available in the art, additional therapeutic compounds are desired that are designed to work alone, sequentially to, or jointly with Apoptin, especially in those cases wherein p53 is (partly) non-functional.

The invention provides novel therapeutic possibilities, for example novel combinatorial therapies or novel therapeutic compounds that can work alone, sequentially to, or jointly with Apoptin, especially in those cases wherein p53 is (partly) non-functional.

BRIEF DESCRIPTION OF THE DRAWINGS

FIG. 1 shows the partial sequence of vector pMT2SM-AAP-4. The DNA sequence of the AAP-4 cDNA starts at position 12 of the DNA sequence and is indicated as "start AAP4 cDNA."

FIG. 2 shows the amino-acid sequence of the analysed region of the Apoptin-associating clone AAP-4 (bold). In addition, the three C-terminal amino acids H-E-G of the multiple cloning site of pACT are given to illustrate that the AAP-4 amino acid sequence is in frame with the GAL4-activation domain. This feature proves that the AAP-4 region is indeed synthesised in yeast cells.

FIG. 3 shows the apoptotic activity of AAP-4 protein and/or Apoptin in human osteosarcoma-derived Saos-2 cells and in human osteosarcoma U2OS cells. (−): no apoptotic activity; (++): strong apoptotic activity; (+++): very strong apoptotic activity. In total three independent experiments have been carried out for both cell types.

FIG. 5 shows the nucleic acid sequence of full-length AAP-4.

FIG. 6 shows the amino acid sequence deduced from the nucleic acid sequence of FIG. 5.

FIG. 7 shows the SET domain of the AAP-4 protein.

DESCRIPTION OF THE PREFERRED EMBODIMENTS

Figure 4:
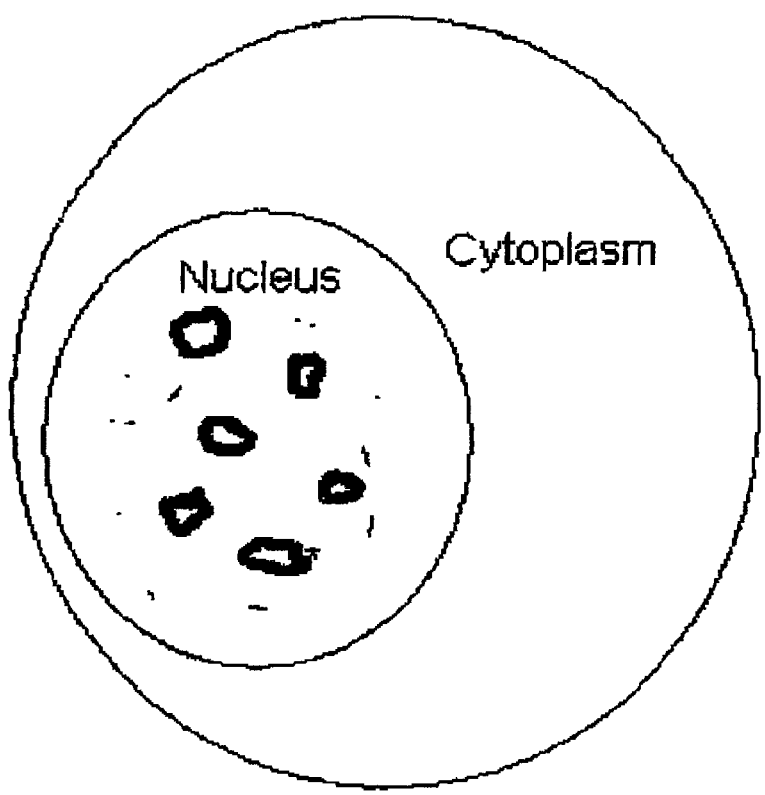
FIG. 4 shows a schematic representation of the nuclear "circular" apoptotic structures containing AAP-4 protein, which are visible in human tumor cells undergoing apoptosis.

In a first embodiment, the invention provides an isolated or recombinant nucleic acid or functional equivalent or fragment thereof encoding an Apoptin-associating proteinaceous substance capable of nuclear localisation, or nuclear co-localisation with Apoptin, and is capable of providing apoptosis, alone or in combination with other apoptosis inducing substances, such as Apoptin, particularly in transformed cells or tumorous cells. In a preferred embodiment it co-localizes with chromatin/DNA structures in the nucleus of the cell, in an initial apoptotic phase leading up to segmentation of the nucleus, condensation and cleavage of DNA into fragments, in most of said cells followed by internucleosomal degradation. In another preferred embodiment of the invention, said substance allows co-localisation which takes place in a somewhat organised pattern whereby circular structures are formed in said nucleus, particularly in an area of the nucleus containing heterochromatin. However, during the above described apoptotic segmentation of the nucleus by condensation and cleavage of DNA into fragments, the euchromatin is of course also effected.

Proteinaceous substance herein is defined as a substance comprising a peptide, polypeptide or protein, optionally having been modified by for example glycosylation, myristilation, phosphorylation, the addition of lipids, by homologous or heterologous di-or multimerisation, or any other (posttranslational) modifications known in the art.

Apoptin-associating herein is defined as belonging to the cascade of substances specifically involved in the cascade of events found in the apoptosis pathway as inducable by Apoptin, preferably those substances that are specifically involved in the p53-independent apoptosis pathway.

In a preferred embodiment, the invention provides an isolated or recombinant nucleic acid or functional equivalent or fragment thereof encoding an Apoptin-associating proteinaceous substance capable of providing apoptosis derived from a cDNA library, preferably a vertebrate cDNA library, such as derivable from poultry, but more preferably a mammalian cDNA library, preferably wherein said cDNA library comprises human cDNA. An Apoptin-associating proteinaceous substance obtained by determining a vertebrate analogue (preferably human) of an Apoptin-associating proteinaceous substance derived from an invertebrate cDNA library is also included.

In another embodiment, the invention provides an isolated or recombinant nucleic acid or functional equivalent or fragment thereof encoding an Apoptin-associating proteinaceous substance capable of providing apoptosis capable of hybridising to a nucleic acid molecule encoding an Apoptin-associating proteinaceous substance capable of providing apoptosis as shown in FIG. 1 or 5, in particular encoding a novel protein capable of providing apoptosis or functional equivalent or functional fragment thereof called Apoptin-associating protein 4, abbreviated herein also as AAP-4. FIG. 1 shows an approximately 750 bp fragment of the complete AAP-4 fragment as depicted in FIG. 5. Both nucleotide sequences encode a protein with at least the capability of binding to Apoptin and providing apoptosis. Of course, an isolated or recombinant nucleic acid or functional equivalent or fragment thereof encoding an additional Apoptin-associating proteinaceous substance capable of associating with the partial or complete AAP-4 protein are herewith also provided, means and methods to arrive at such an additional protein located in the Apoptin cascade follow in the detailed description given herein. Knowledge derived from studying the partial or full-length AAP-4 is exploited to determine a functional pathway in which partial or full-length AAP-4 is involved, thus allowing the design of a therapeutic means of intervention in such a pathway.

In particular, the invention provides an isolated or recombinant nucleic acid or functional equivalent or fragment thereof encoding an Apoptin-associating proteinaceous substance capable of providing apoptosis being at least 60% homologous, preferably at least 70%, more preferably at least 80%, even more preferably 90% and most preferably at least 95% homologous to a nucleic acid molecule, or to a functional equivalent or functional fragment thereof, encoding an Apoptin-associating proteinaceous substance as shown in FIG. 1 or 5.

Furthermore, the invention provides a vector comprising a nucleic acid according to the invention. Examples of such a vector are given in the detailed description given herein; such as vector pMT2SM-AAP-4, pMT2SM vector expressing Myc-tagged AAP-4 cDNA, a plasmid expressing an Apoptin-associating protein fragment, and so on. These and other vectors are for example useful in finding additional Apoptin-associating proteinaceous substances from the cascade, as defined above.

In yet another embodiment, the invention provides a vector comprising a nucleic acid according to the invention, said vector comprising a gene-delivery vehicle, making the invention very useful in gene therapy. By equiping a gene delivery vehicle with a nucleic acid according to the invention, and by targeting said vehicle to a cell or cells that have been over-proliferating and/or have shown decreased death rates, said gene delivery vehicle provides said cell or cells with the necessary means for apoptosis, providing far reaching therapeutic possibilities.

Furthermore, the invention provides a host cell comprising a nucleic acid or a vector according to the invention. Examples comprise transformed or transfected bacterial or yeast cells as described in the detailed description herein. Preferred is a host cell according to the invention which is a transformed eukaryotic cell such as a yeast cell or a vertebrate cell, such as mammalian or Cos cells transformed or transfected with a nucleic acid or vector according to the invention. Said cells are in general capable to express or produce a proteinaceous substance capable of providing apoptosis with the ability to associate with Apoptin.

The invention furthermore provides an isolated or recombinant Apoptin-associating proteinaceous substance capable of providing apoptosis. As for example shown herein in FIG. 3, expression of such Apoptin-associating proteinaceous substance in cells, such as tumour cells, or other over-proliferating cells, induces the apoptotic process. It can do so alone, or in the presence of other apoptosis inducing substances such as Apoptin, and especially so independent of p53, showing that also in those cases where (functional) p53 is absent apoptosis can be induced by a substance according to the invention. In particular, the invention provides a proteinaceous substance according to the invention encoded by a nucleic acid according to the invention, for example comprising at least a part of an amino acid sequence as shown in FIGS. 2 or 6 or a functional equivalent or functional fragment thereof capable of providing apoptosis alone or in combination, preferably co-localising, with other apoptosis inducing substances such as Apoptin (see for example FIG. 4, where circular structures are shown where Apoptin and a substance as provided were found to co-localise in transformed or tumorous cells).

The invention also provides an isolated or synthetic antibody specifically recognising a proteinaceous substance or functional equivalent or functional fragment thereof according to the invention. Such an antibody is for example obtainable by immunising an experimental animal with a Apoptin-associating proteinaceous substance or an immunogenic fragment or equivalent thereof and harvesting polyclonal antibodies from said immunised animal (as shown herein in the detailed description), or obtainable by other methods known in the art such as by producing monoclonal antibodies, or (single chain) antibodies or binding proteins expressed from recombinant nucleic acid derived from a nucleic acid library, for example obtainable via phage display techniques.

With such an antibody, the invention also provides a proteinaceous substance specifically recognisable by such an antibody according to the invention, for example obtainable via immunoprecipitation, Western Blotting, or other immunological techniques known in the art.

Furthermore, the invention provides use of a nucleic acid, vector, host cell, or proteinaceous substance according to the invention for the induction of apoptosis, as for example shown in FIG. 3. In particular, such use is provided wherein said apoptosis is p53-independent. In particular, such use is also provided further comprising use of a nucleic acid encoding Apoptin or a functional equivalent or fragment thereof or use of Apoptin or a functional equivalent or fragment thereof. As can be seen from FIG. 3, combining these Apoptin-inducing substances increases the percentage apoptosis of treated tumour cells.

Such use as provided by the invention is particularly useful from a therapeutic viewpoint. The invention provides herewith a pharmaceutical composition comprising a nucleic acid, vector, host cell, or proteinaceous substance according to the invention. In addition, such a pharmaceutical composition according to the invention is provided further comprising a nucleic acid encoding Apoptin or a functional equivalent or fragment thereof or Apoptin or a functional equivalent or fragment thereof.

Such a pharmaceutical composition is in particular provided for the induction of apoptosis, for example wherein said apoptosis is p53-independent, for the treatment of a disease where enhanced cell proliferation or decreased cell death is observed, as is in general the case when said disease comprises cancer or auto-immune disease. Herewith the invention provides a method for treating an individual carrying a disease where enhanced cell proliferation or decreased cell death is observed comprising treating said individual with a pharmaceutical composition according to the invention. In particular these compositions comprise a factor of an apoptosis pathway, which is specific for transformed cells and cancer-prone cells. Therefore, these compositions are essential for new treatments, but also for diagnosis of diseases related with aberrance's in the apoptotic process, such as cancer and auto-immune diseases.

Furthermore, the invention provides for diagnosis of cancer-prone cells in particular by detecting those cells that under influence of a substance (e.g. by transfection) as provided by the invention show condensing of chromatin/DNA or circular structures as described in FIG. 4.

The invention also provides an isolated or recombinant nucleic acid encoding a proteinaceous substance comprising the amino acid sequence as shown in FIG. 7.

In a further embodiment the invention provides an assay to identify a putative effector of the activity of the proteinaceous substance encoded by a nucleic acid as shown in FIG. 5 comprising bringing in contact a proteinaceous substance comprising amino acid 852-900 of the amino acid sequence shown in FIG. 6 with said effector and determining the binding of said effector.

The following examples are offered by way of illustration of the present invention, not limitation.

EXPERIMENTAL

We have used the yeast-2 hybrid system (Durfee et al., 1993) to identify Apoptin-associating cellular compounds, which are essential in the induction of apoptosis. The used system is an in vivo strategy to identify human proteins capable of physically associating with Apoptin. It has been used to screen cDNA libraries for clones encoding proteins capable of binding to a protein of interest (Fields and Song, 1989, Yang et al., 1992). The invention provides for example a novel Apoptin-associating protein, one of which is named Apoptin-associating protein 4 abbreviated as AAP-4. The invention also provides a method for inducing apoptosis through interference with the function of this newly discovered AAP-4 protein or functional equivalents or fragments thereof and/or the induction of apoptosis by means of (over)expression of AAP-4 or related gene or functional equivalents or fragments thereof.

The invention also provides an anti-tumor therapy based on the interference with the function of AAP-4-like proteins and/or its (over)expression. An aberrantly high level of AAP-4-like proteins will result in the induction of the opposite process of cell transformation, namely apoptosis. The invention furthermore provides the mediator of Apoptin-induced apoptosis, which is tumor-specific. The invention provides a therapy for cancer, auto-immune diseases or related diseases which is based on AAP-4-like proteins alone or in combination with Apoptin and/or Apoptin-like compounds.

Construction of pGBT9-VP3

For the construction of the bait plasmid, which enables the identification of Apoptin-associating proteins by means of a yeast-two-hybrid system, plasmid pET-16b-VP3 (Noteborn, unpublished results) was treated with NdeI and BamHI. The 0.4 kb NdeI-BamHI DNA fragment was isolated from low-melting-point agarose. Plasmid pGBT9 (Clontech Laboratories, Inc, Palo Alto, USA) was treated with the restriction enzymes EcoRI and BamHI. The about 5.4-kb DNA fragment was isolated and ligated to an EcoRI-NdeI linker and the 0.4-kb DNA fragment containing the Apoptin-encoding sequences starting from its own ATG-initiation codon. The final construct containing a fusion gene of the GAL4-binding domain sequence and Apoptin under the regulation of the yeast promoter ADH was called pGBT-VP3 and was proven to be correct by restriction-enzyme analysis and DNA-sequencing according to the Sanger method (1977).

All cloning steps were essentially carried out as described by Maniatis et al. (1992). The plasmid pGBT-VP3 was purified by centrifugation in a CsCl gradient and column chromatography in Sephacryl S500 (Pharmacia).

GAL4-Activation Domain-Tagged cDNA Library

The expression vector pACT, containing the cDNAs from Epstein-Barr-virus-transformed human B cells fused to the GAL4 transcriptional activation domain, was used for detecting Apoptin-associating proteins. The pACT c-DNA library is derived from the lambda-ACT cDNA library, as described by Durfee et al. 1993.

Bacterial and Yeast Strains

The *E.coli* strain JM109 was the transformation recipient for the plasmid pGBT9 and pGBT-VP3. The bacterial strain electromax/DH10B was used for the transformation needed for the recovery of the Apoptin-associating pACT-cDNAs, and was obtained from GIBCO-BRL, USA.

The yeast strain Y190 was used for screening the cDNA library, and all other transformations, which are part of the used yeast-two-hybrid system.

Media

For drug selections Luria Broth (LB) plates for *E.coli* were supplemented with ampicillin (50 microgram per ml). Yeast YPD and SC media were prepared as described by Rose et al. (1990).

Transformation of Competent Yeast Strain Y190 with Plasmids pGBT-VP3 and pACT-cDNA and Screening for Beta-Galactosidase Activity The yeast strain Y190 was made competent and transformed according to the methods described by Klebe et al. (1983). The yeast cells were first transformed with pGBT-VP3 and subsequently transformed with pACT-cDNA, and these transformed yeast cells were grown on histidine-minus plates, also lacking leucine and tryptophan.

Hybond-N filters were placed on yeast colonies, which were histidine-positive and allowed to wet completely. The filters were lifted and submerged in liquid nitrogen to permeabilize the yeast cells. The filters were thawed and layed with the colony side up on Whattman 3MM paper in a petridish with Z-buffer (Per liter: 16.1 gr $Na_2HPO_4.7H_2O$, 5.5 gr $NaH_2PO_4.H_2O$, 0.75 gr KCl and 0,246 gr $MgSO_4.7H_2O$, pH 7.0) containing 0.27% beta-mercaptoethanol and 1 mg/ml X-gal. The filters were incubated for at least 15 minutes or during night.

Recovery of Plasmids from Yeast

Total DNA from yeast cells, which were histidine- and beta-galactosidase-positive, was prepared by using the glusulase-alkaline lysis method as described by Hoffman and Winston (1987) and used to transform Electromax/DH10B bacteria via electroporation using a Bio-Rad GenePulser according the manufacturer's specifications.

Transformants were plated on LB media containing the antibiotic agent ampicillin.

Isolation of Apoptin-Associating pACT Clones

By means of colony-filter assay the colonies were lysed and hybridized to a radioactive-labeled 17-mer oligomer, which is specific for pACT (see also section Sequence analysis). Plasmid DNA was isolated from the pACT-clones, and by means of XhoI digestion analysed for the presence of a cDNA insert.

Sequence Analysis

The subclone containing the sequence encoding Apoptin-associating protein was partially sequenced using dideoxy NTPs according to the Sanger-method, which was performed by Eurogentec, Seraing, Belgium). The used sequencing primer was a pACT-specific 17-mer comprising of the DNA-sequence 5'-TACCACTACAATGGATG-3' SEQ ID NO: 1.

The sequences of the Apoptin-associating cDNAs were compared with known gene sequences from the EMBL/Genbank.

Generation and Testing of Antibodies

In order to generate polyclonal antisera against the AAP-4 protein, we designed three peptides. These peptides were:

1) EESTPVHDSPGKDDA SEQ ID NO: 2

2) DSFKTKDSFRTAKSK SEQ ID NO: 3

3) IDIDISSRRREDQSL SEQ ID NO: 4

These peptides were synthesized at Eurogentec (Belgium) with the standard addition of a C-terminal cysteine residue and all subsequent antibody syntheses was also performed there. These peptides were coupled to Keyhole Limpet Hemocyanin (KLH) and injected as a cocktail into two specific pathogen free rabbits with an immunization schedule of one injection and three subsequent boosts. Blood samples were taken before and after immunization. The sera were tested in-house for specific reactivity to the peptide cocktail by ELISA. The titers from each rabbit were high (>200,000). Furthermore, for certain subsequent purposes, the AAP-4 antibody was immune-purified using peptide cocktail coupled to immobilized diaminodipropylamine agarose columns (Pierce) according to the manufacturer's protocol.

The best AAP-4 antibody preparation of the two generated was selected for further use. We tested the efficacy of this antibody by transfecting 6 cm plates of sub-confluent primate COS-7 and human U2OS cells using the calcium phosphate co-precipitation method with 5 ug of the AAP-4-myc construct, and as a control, untransfected cells. Two days post-transfection, cells were washed briefly in PBS, lysed in RIPA buffer (10 mM Tris 7.5, 150 mM NaCl, 0.1% SDS, 1.0% NP-49 and 1.0% sodium deoxycholate), clarified by centrifugation, and the supernatant fractionated on SDS-denaturing polyacrylamide gel electrophoresis. Proteins were Western-transferred to PVDF membranes (Immobilon, Millipore) using standard methodology. Membranes were blocked in 5% non-fat dry milk in tris-buffered saline containing 0.1% Tween-20, then incubated in the unpurified AAP-4 antisera at a concentration of 1:5000. After a brief wash, membranes were further incubated in HRP-conjugated goat-anti-rabbit Ig at a concentration of 1:2000. After a thorough series of wash steps, proteins were detected using enhanced chemiluminescence (Amersham) according to the manufacturer's protocol, and exposed to x-ray film and developed using standard automated machinery.

In addition, we tested the purified AAP-4 antibody using immunoprecipitation in a manner the same as above, except that after centrifugation, the supernatant was added to 10 ul of AAP-4 antibody pre-coupled to protein-A-sepharose beads, incubated for 1 hour with tumbling, then washed before fractionation on SDS-PAGE gels and Western analysis. Detection in this case was performed with the anti-myc tag monoclonal antibody 9E10 (Evan et al. 1985).

Finally, the purified antibody was tested for utility in immunofluorescence by including glass coverslips in the above transfections. Coverslips were fixed with 4% paraformaldehyde, blocked with normal goat serum, incubated in AAP-4 antibody diluted 1:5, washed, incubated in FITC-conjugated goat-anti-rabbit Ig, mounted and visualized under fluorescence microscopy.

Northern Blot Analysis

To examine whether AAP-4 was differentially expressed in tumor versus normal tissue, we tested a commercially-available Northern blot (Invitrogen, cat. No. #D310001) that contained tumor and normal tissue derived from the same patient, from a variety of tissue types. The DNA probe was derived from an internal HindIII fragment of AAP-4 and was labelled with $^{32}$P-dATP using the MegaPrime kit of Amersham. All prehybridization, hybridization and washing steps were done according to the Northern blot manufacturer's recommendation. Further guidance for hybridization conditions is provided in *Molecular Cloning, A Laboratory Manual*, by Sambrook, et al (1989), published by Cold Spring Harbor Laboratory Press. Blots were subjected to autoradiography and developed using standard automated methods.

Cloning of Full-Length AAP-4

A human brain cDNA library was obtained from Clontech (Marathon-Ready™ cDNA). The cDNA for AAP-4 was generated in a RACE-PCR (Rapid Amplification of cDNA ends) according to the manufacturer's instructions included in the Marathon-Ready™ cDNA kit. For the RACE-PCR the following "touch-down" program was used in a Perkin-Elmer 9600 thermocycler: 1 cycle 94° C. 30 sec; 5 cycles of 94° C. 5 sec; 72° C. 3 min; 5 cycles of 94° C. 5 sec; 70° C. 3 min; 25 cycles of 94° C. 5 sec; 68° C. 3 min. The sequences of the AAP-4 primers used in the RACE reaction were:

```
AAP-4#3F  5' GTC AGC TCT AAC ACT GAT GCA GAT ACC AC 3'   SEQ ID NO: 5

AAP-4#3R  5' GTG GTA TCT GCA TCA GTG TTA GAG CTG AC 3'   SEQ ID NO: 6
```

The RACE products were cloned in the pCR®4-TOPO vector according to the instructions of the TOPO-TA cloning kit from Invitrogen. The sequences of the cloned PCR products were amplified with the Applied Biosystem (ABI) Prism®BigDye™ Terminator sequencing kit and analysed in the ABI 310 capillary sequencer. The complete open reading frame (ORF) of AAP-4 was subsequently amplified in the following PCR reaction 1 cycle 94° C. 30 sec; 30 cycles 94° C. 5 sec, 68° C. 3 min. The gene-specific primers had the following sequences:

```
AAP-4#8F  5' GAG AGT GAC TAA ATG CAC CTG GGT CAG G 3'   SEQ ID NO: 7

AAP-4#9R  5' GTT ATC CCA GGT CAA GTT AAG ACC 3'         SEQ ID NO: 8
```

The full-length generated product cloned into the pCR®4-TOPO vector was subjected to a final sequence analysis as previously described.

Results and Discussion

Apoptin induces apoptosis specifically in transformed cells, such as cell lines derived from human tumors. To identify the essential compounds in this cell-transformation-specific and/or tumor-specific apoptosis pathway, a yeast genetic screen was carried out.

We have used a human cDNA library, which is based on the plasmid vector pACT containing the complete cDNA copies made from Epstein-Barr virus-transformed human B cells (Durfee et al., 1993).

Construction of a Bait Plasmid Expressing a Fusion Gene Product of GAL4-DNA-Binding Domain and Apoptin To examine the existence of Apoptin-associating proteins in the human transformed/tumorigenic cDNA library, a so-called bait plasmid had to be constructed. To that end, the complete Apoptin-encoding region, flanked by about 40 basepairs downstream from the Apoptin gene, was cloned in the multiple cloning site of plasmid pGBT9.

The final construct, called pGBT-VP3, was analysed by restriction-enzyme analysis and sequencing of the fusion area between Apoptin and the GAL4-DNA-binding domain.

A Gene(Fragment) Encoding an Apoptin-Associating Protein is Determined by Transactivation of a GAL4-Responsive Promoter in Yeast.

The Apoptin gene was fused to the GAL4-DNA-binding domain of plasmid pGBT-VP3, whereas all cDNAs derived from the transformed human B cells are fused to the GAL4-activation domain of plasmid pACT. If one of the proteinaceous substances encoded by said cDNAs binds to Apoptin, the GAL4-DNA-binding domain would be in the vicinity of the GAL4-activation domain resulting in the activation of the GAL4-responsive promoter, which regulates the reporter genes HIS3 and LacZ.

The yeast clones containing plasmid expressing Apoptin and a plasmid expressing an Apoptin-associating protein fragment can grow on a histidine-minus medium and will stain blue in a beta-galactosidase assay. Subsequently, the plasmid with the cDNA insert encoding the Apoptin-associating protein can be isolated and characterized.

Before we did so, however, we determined that transformation of yeast cells with pGBT-VP3 plasmid alone, or in combination with an empty pACT vector, did not result in the activation of the GAL4-responsive promoter.

Identification of Apoptin-Associating Protein Encoded by cDNA Derived from a Human Transformed B Cell Line.

We have found one yeast colony that upon transformation with pGBT-VP3 and pACT-cDNA was able to grow on a histidine-minus medium (also lacking leucine and tryptophan) and stained blue in a beta-galactosidase assay. These results indicate that the observed yeast colony contained besides the bait plasmid pGBT-VP3 also a pACT plasmid encoding a potential Apoptin-associating protein.

Plasmid DNA was isolated from the positive yeast colony and transformed in bacteria. By means of a filter-hybridization assay using a pACT-specific labeled DNA-probe, the clone containing pACT plasmid could be determined.

Subsequently, pACT DNA was isolated and digested with restriction enzyme XhoI, which resulted in the presence of a 2.1-kbp cDNA insert. Finally, the insert of pACT plasmid containing the cDNA insert was fully sequenced by using the Sanger method (Sanger et al., 1977).

Description of Apoptin-Associating Proteins

The yeast genetic screen for Apoptin-associating proteins resulted in the detection of a cDNA clone comprising a single type of protein, namely a novel protein called Apoptin-associating protein 4, abbreviated as AAP-4.

The determined DNA sequence part of the AAP-4 cDNA clone is shown in FIG. 1. The amino acid sequence, derived from the detected DNA sequence of clone AAP-4 is given in FIG. 2.-

Construction of an Expression Construct for the Identification of AAP-4 Protein in Mammalian Cells.

To study whether the cloned cDNA AAP-4 indeed encodes (Apoptin-associating) a protein product, we carried out the following experiments.

The DNA plasmid pMT2SM contains the adenovirus 5 major late promoter (MLP) and the SV40 ori enabling high levels of expression of foreign genes in transformed mammalian cells, such as SV-40 transformed Cos cells. Furthermore, the pMT2SM vector contains a Myc-tag (amino acids: EQKLISEEDL SEQ ID NO: 9) which is in-frame with the foreign gene product. This Myc-tag enables the recognition of e.g. Apoptin-associating proteins by means of the Myc-tag-specific 9E10 antibody.

The pMT2SM vector expressing Myc-tagged AAP-4 cDNA was constructed as follows. The pACT-AAP-4 cDNA clone was digested with the restriction enzyme XhoI and the cDNA insert was isolated. The expression vector pMT2SM was digested with XhoI and treated with calf intestine alkline phosphatase and ligated to the isolated AAP-4 cDNA inserts. By sequence analysis, the pMT2SM constructs containing the AAP-4 cDNA in the correct orientation were identified.

The synthesis of Myc-tagged AAP-4 protein was analyzed by transfection of Cos cells with plasmid pMT2SM-AAP-4. As negative control, Cos cells were mock-transfected. Two days after transfection, the cells were lysed and Western-blot analysis was carried out using the Myc-tag-specific antibody 9E10.

The Cos cells transfected with pMT2SM-AAP-4 were proven to synthesize a specific Myc-tagged AAP-4 product with the size of approximately 60-65 kDa. As expected, the lysates of the mock-transfected Cos cells did not contain a protein product reacting with the Myc-tag-specific antibodies.

These results indicate that we have been able to isolate a cDNA that is able to produce a protein product with the ability to associate to the apoptosis-inducing protein Apoptin.

Co-immunoprecipitation of Myc-tagged AAP-4 Protein with Apoptin in a Transformed Mammalian Cell System.

Next, we have analysed the association of Apoptin and the AAP-4 protein by means of co-immunoprecipitations using the Myc-tag-specific antibody 9E10. The 9E10 antibodies were shown not to bind directly to Apoptin, which enables the use of 9E10 for carrying out co-immuno-precipitations with (myc-tagged) Apoptin-associating proteins and Apoptin.

To that end, Cos cells were co-transfected with plasmid pCMV-VP3 encoding Apoptin and with plasmid pMT2SM-AAP-4. As a negative control, cells were transfected with pCMV-VP3 expressing Apoptin and a plasmid pcDNA3.1.LacZ-myc/His-LacZ encoding the myc-tagged beta-galactosidase, which does not associate with Apoptin.

Two days after transfection, the cells were lysed in a buffer consisting of 50 mM Tris (7.5), 250 mM NaCl, 5 mM EDTA, 0.1% Triton X100, 1 mg/ml $Na_4P_2O_7$ and freshly added protease inhibitors such as PMSF, Trypsin-inhibitor, Leupeptine and $Na_3VO_4$. The specific proteins were immuno-precipitated as described by Noteborn et al. (1998) using the Myc-tag-specific antibodies 9E10, and analyzed by Western blotting.

Staining of the Western blot with 9E10 antibodies and 111.3 antibodies, which are specifically directed against myc-tag and Apoptin, respectively, showed that the "total" cell lysates contained the 16-kDa Apoptin product and the Myc-tagged AAP-4 protein or beta-galactosidase product. Immunoprecipitation of the Myc-tagged AAP-4 products was accompanied by the immuno-precipatation of Apoptin product of 16 kDa. In contrast, immunoprecipitation of myc-tagged beta-galactosidase did not result in a significant co-precipitation of the Apoptin protein. In addition, immunoprecipitation of the Apoptin protein, by means of a polyclonal antibody directed against the C-terminal part of Apoptin (Noteborn and Danen, unpublished results), was accompanied by the immunoprecipitation of the myc-tagged AAP-4 product of 60-65 kDa.

In total, three independent immunoprecipitation experiments were carried out, which all showed the associating ability of Apoptin to the AAP-4 protein.

These results indicate that the novel determined AAP-4 protein is able to specifically associate with Apoptin not only in the yeast background, but also in a mammalian transformed cellular system.

Over-Expression of the Novel AAP-4 Protein in Human Osteosarcoma Saos-2 Cells, Lacking Functional p53, Induces the Apoptotic Process.

We have examined whether AAP-4 carries apoptotic activity in Saos-2 cells. First, we have analysed the cellular localisation of the novel AAP-4 protein in human transformed cells. To that end, the human osteosarcoma-derived Saos-2 cells were transfected, as described by Danen-van Oorschot (1997), with plasmid pMT2SM-AAP-4 encoding the myc-tagged AAP-4 protein, respectively.

By indirect immunofluorescence using the myc-tag-specific antibody 9E10 and DAPI, which stains the nuclear DNA, it was shown that AAP-4 protein was present in the nucleus of the cell. Most often it co-localizes with the chromatin/DNA structures.

During tumor development, most of the tumors will lack functional tumor suppressor p53. Tumor cells lacking functional p53 are in general poor responders to (chemo)therapeutic agents. Therefore, it is of importance to prove whether AAP-4 can induce apoptosis in human tumor cells in the absence of functional p53.

To this end we examined whether (over)-expression of AAP-4 protein results in induction of apoptosis. Four days after transfection, the majority of AAP-4-positive cells were aberrantly stained with DAPI, which is indicative for induction of apoptosis (Telford, 1992, Danen-van Oorschot, 1997). Cells expressing Apoptin also underwent apoptosis, albeit slightly less than the AAP-4-producing cells, whereas as expected the cells synthesizing the non-apoptotic beta-galactosidase (LacZ) protein did not. The results are shown in FIG. 3.

Co-expression of Apoptin and AAP-4 protein in human tumor cells, such as Saos-2 cells, results in a faster apoptotic process as expression of Apoptin or AAP-4 protein alone (FIG. 3).

The fact that AAP-4 protein can induce apoptosis in p53-minus Saos-2 cells indicates that AAP-4 can induce p53-independent apoptosis. These results imply that AAP-4 can be used as anti-tumor agent in cases where other (chemo)therapeutic agents will fail. Furthermore, the finding that both Apoptin and AAP-4 induce a p53-independent pathway indicates that AAP-4 fits in the Apoptin-induced apoptotic pathway.

In conclusion, we have identified an Apoptin-associating protein, namely the novel AAP-4 protein, which is present in the nucleus and able to induce (p53-independent) apoptosis in human tumor cells.

Over-Expression of the Novel AAP-4 Protein in Human Osteosarcoma U2OS Cells, Expressing Wild-Type p53, Induces the Apoptotic Process.

We were also interested in examining the activity of AAP-4 in an additional cell line. To this end we have transfected human osteosarcoma-derived U2OS cells expressing wild-type p53 with plasmid pMT2SM-AAP-4 encoding the myc-tagged AAP-4 protein. As control, U2OS cells were transfected with the plasmid pCMV-LacZ encoding myc-tagged LacZ. Four or five days after transfection, the cells were fixed and analysed for myc-tagged AAP-4 expression by means of immunofluorescence using the myc-tag specific antibody 9E10 and for apoptotic activity by DAPI staining. U2OS cells were stained aberrantly with DAPI whereas the cells containing myc-tagged LacZ were not, which is indicative for induction of AAP-4-specific apoptosis.

These experiments were repeated three times and clearly showed that AAP-4 alone also kills U2OS tumor cells (FIG. 3). Thus absence or presence of p53 is irrelevant for AAP-4 activity (like Apoptin), which broadens the tumor-target spectrum of AAP-4.

AAP-4 localizes in Apoptotic Structures.

One of the striking features of CAV-induced apoptosis is the "circular" Apoptin-positive structures occurring during the apoptotic process (Noteborn et al., 1994). These structures are visible in the nucleus at an early time point during apoptosis and become at a later stage more and more pronouncedly structured as circles or circular appearances or structures. We have now found that AAP-4 is located in the same "circular" structures as described for Apoptin. We have analyzed cells co-expressing both (myc-tagged) AAP-4 and Apoptin. Saos-2 cells were co-transfected with pMT2SN-AAP-4 and pCMV-Apoptin (Danen-van Oorschot, 1997). Indirect immunofluorescence, using both antibodies detecting AAP-4 or Apoptin and FITC- or rhodamine-labeled secondary antibody conjugates was carried out as described by Danen-van Oorschot, 1997a, proved that the "circular" structures contain both Apoptin and AAP-4 protein. Within these structures, Apoptin and AAP-4 partially co-localize with each other. It is the first cellular (derived from human (tumor) cells) protein that is associated with CAV- and/or Apoptin-associated apoptotic structures. A schematic representation of these structures is given in FIG. 4.

When AAP-4 was expressed alone in Saos-2 tumor cells, the staining pattern was diffusely punctuate nuclear staining in addition to large circular structures that lacked staining, giving the appearance of black holes in the nucleus. In contrast, normal VH10 cells expressing the AAP-4 construct showed only the diffuse nuclear staining, with no evidence for such black holes. These results strongly suggest a tumor-specific distribution of AAP-4 in the absence of Apoptin.

In conclusion, we have provided evidence that interference of specific factors with the function of AAP-4 proteins results in induction of apoptosis. Therapies based on induction of (p53-independent) apoptosis are possible utilising the interference with the function of AAP-4 proteins. An example of such an interfering factor is Apoptin. Another CAV-derived protein, which is known to induce apoptosis and also known to enhance Apoptin activity is VP2 (Noteborn et al., 1997).

Utility of AAP-4 Antisera

The best AAP-4 antibody of the two generated was selected for further use. We tested the efficacy of this antibody by transfecting primate COS-7 and human U2OS cells with the AAP-4-myc construct. Western analysis showed that the approximately 60-65 kDa AAP-4-myc protein was detected strongly only in samples where the DNA was transfected. Similarly, in immunoprecipitation experiments, AAP-4-myc was also strongly detected. Finally, we could detect the presence of AAP-4 in the nucleus using this AAP-4 antibody in immunofluorescence analysis.

Northern Blot Analysis

To examine whether AAP-4 was differentially expressed in tumor versus normal tissue, we tested a commercially-available Northern blot (Invitrogen, cat. No. #D310001) that contained tumor and normal tissue derived from the same patient, from a variety of tissue types.

There was a very large RNA, approximately 6 to 7 kb, expressed in normal brain tissue that was not present in the same amount of RNA from uninvolved brain of the same patient. However, in the normal brain sample we saw much smaller faint bands that might indicate the presence of splice variants.

Cloning and Sequence Analysis of Full-Length AAP-4

A further sequence analysis of the human AAP-4 DNA sequence yielded the 5690 bp long nucleic acid sequence given in FIG. 5. An open reading frame was found in this nucleic acid sequence at position 236 to 2866. The deduced amino acid sequence is given in FIG. 6.

A protein domain called SET-domain was found in the amino acid sequence of the human AAP-4 protein. It spans the region of the amino acid 185 to amino acid 304.

The SET domain is a 130-amino acid, evolutionarily conserved sequence motif present in chromosomal proteins that function in modulating gene activities from yeast to mammals. Initially identified as members of the Polycomb- and trithorax-group (Pc-G and trx-G) gene families, these genes regulate the expression of the homeotic genes through a mechanism thought to involve some aspect of chromatin structure. Other proteins which have this motif also have additional domains or characteristics that support that suggestion that the SET domain is involved in chromatin-mediated gene regulation, and possibly in determining chromosome architecture. These observations implicate SET domain proteins as multifunctional chromatin regulators with activities in both eu- and heterochromatin (T. Jenuwein et al. 1998, Cell. Mol. Life Sci. 54, 80-93).

Recently, it has been demonstrated that SET domains are protein-protein interaction domains important for the activity of multicomponent complexes involved in transcriptional activation or repression or phosphorylation (T. Rozovskaia et al 2000, Oncogene 19, 351-357). SET domains are found in a number of proteins closely associated with human tumorigenesis such as HRX/ALL1/MLL/Htrx, MOZ and MMSET all of which are part of aberrant fusion proteins derived from chromosomal translocations found in a high percentage of human leukemias (S.Jacobson and L. Pillus 1999, Curr. Opinion in Gen & Dev. 9, 175-184).

It was not until the present invention that such a SET domain was identified in an Apoptin associating protein and therefore, affecting the functional activity of the SET domain of AAP-4 should have therapeutic effects against tumors. The SET domain can be used to identify substances which bind to the SET domain. This would be done by methods known to persons skilled in the art, e.g. by binding studies, where an AAP-4 peptide comprising the SET domain is bound to a matrix and it is tested whether test substances bind to the AAP-4 peptide, or by co-immnuno-precipitation of an AAP-4 peptide comprising the SET domain with test substances using antibodies generated against the AAP-4 peptide comprising the SET domain. Test substances are for example small organic compounds derived e.g. from a compound library or peptides or proteins derived e.g. from a peptide library or from a natural source like a cell extract. The test substances are for example labelled for easier detection. The substances found to bind to the SET domain can either enhance or inhibit one or more effects of AAP-4. This is tested by measuring the apoptotic activity of AAP-4 as described above in the presence of said substances and by determining the nuclear localization of AAP-4 as described above in the presence of said substances.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

REFERENCES

1. Bellamy, C. O. C., Malcomson, R. D. G., Harrison, D. J., and Wyllie, H. 1995. Cell death and disease: The biology and regulation of apoptosis. Seminars in Cancer Biology 6, 3-12.
2. Danen-Van Oorschot, A. A. A. M., Fischer, D. F., Grimbergen, J. M., Klein, B., Zhuang, S. -M., Falkenburg, J. H. F., Backendorf, C., Quax, P. H. A., Van der Eb, J. A., and Noteborn, M. H. M. (1997). Apoptin induces apoptosis in human transformed and malignant cells but not in normal cells. Proceedings National Academy Sciences, USA: 94, 5843-5847.
3. Danen-Van Oorschot, A. A. A. M, Den Hollander, A., Takayama, S., Reed, J., Van der Eb, A. J. and Noteborn, M. H. M. (1997a). BAG-1 inhibits p53-induced but not Apoptin-induced apoptosis. Apoptosis 2, 395-402.
4. Duke, R. C., Ocjius, D. M., Young, J, D -E. (1996). Cell suicide in health and disease. Scientific American December 1996, 48-55.
5. Durfee, T., Becherer, K., Chen, P. -L., Yeh,S. -H., Yang, Y., Kilburn, A. E., Lee, W. -H., and Elledge, S. J. (1993). The retinoblastoma protein associates with the protein phosphate type I catalytic subunit. Genes and Development 7, 555-569.
6. Earnshaw, W. C., 1995. Nuclear changes in apoptosis. Current Opinion in Cell Biology 7, 337-343.
7. Fields, S. and Song, O. K. (1989). A novel genetic system to detect protein-protein interactions. Nature 340, 245-246.
8. Hockenberry, D. M. (1994). Bcl-2 in cancer, development and apoptosis. Journal of Cell Science, Supplement 18, 51-55.
9. Hoffman, C. S. and Winston, F. (1987). A ten-minute DNA preparation from yeast efficiently releases autonomous plasmids for transformation of *Escherichia coili*. Gene 57, 267-272.
10. Kerr, J. F. R., Winterford, C. M., and Harmon, B. V. (1994). Apoptosis: Its significance in cancer and cancer therapy. Cancer 73, 2013-2026.
11. Klebe, R. J., Harriss, J. V., Sharp, Z. D., and Douglas, M. G. (1983). A general method for polyethylene-glycol-induced genetic transformation of bacteria and yeast. Gene 25, 333-341.
12. Levine, A. J. (1997). p53, the cellular gatekeeper for growth and division. Cell 88, 323-331.
13. Maniatis, T., Fritsch, E. F., and Sambrook, J. (1982). Molecular Cloning: A Laboratory Manual. CSHL Press, New York, USA.
14. McDonell T. J., Meyn, R. E., Robertson, L. E. (1995). Implications of apoptotic cell death regulation in cancer therapy. Seminars in Cancer Biology 6, 53-60.
15. Noteborn, M. H. M. (1996). PCT application WO 96/41191. Apoptin induces apoptosis in human transformed and malignant cells but not in normal cells as essential characteristic for the development of an anti-tumor therapy.
16. Noteborn, M. H. M., and De Boer, G. F. (1996). U.S. Pat. No. 030, 335.
17. Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131-3139.
18. Noteborn, M. H. M., and Pietersen, A. (1998). A gene delivery vehicle expressing the apoptosis-inducing proteins VP2 and/or Apoptin. PCT Application no. PCT/NL98/00213
19. Noteborn, M. H. M., Todd, D., Verschueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. Journal of Virology 68, 346-351.
20. Noteborn, M. H. M., Verschueren, C. A. J., Koch, G., and Van der Eb, A. J. (1998). Simultaneous expression of recombinant baculovirus-encoded chicken anemia virus (CAV) proteins VP1 and VP2 is required for formation of the CAV-specific neutralizing epitope. Journal General Virology, 79, 3073-3077.
21. Noteborn, M. H. M., and Zhang, Y. (1998). Methods and means for determining the transforming capability of agents, for determining the predisposition of cells to become transformed and prophylactic treatment of cancer using Apoptin-like activity. PCT Application no. PCT/NL98/00457
22. Noteborn, M. H. M., Danen-van Oorschot, A. A. A. M., Van der Eb, A. J. (1998a). Chicken anemia virus: Induction of apoptosis by a single protein of a single-stranded DNA virus. Seminars in Virology 8, 497-504.
23. Paulovich, A. G., Toczyski, D., Hartwell, H. (1997). When checkpoints fail. Cell 88, 315-321.
24 Pietersen, A. M., Van der Eb, M. M., Rademaker, H. J., Van den Wollenberg, D. J. M., Rabelink, M. J. W. E., Kuppen, P. J. K., Van Dierendonck, J. H., Van Ormondt, H., Masman, D., Van de Velde, C. J. H., Van der Eb, Hoeben, R. C., and Noteborn, M. H. M. (1999). Specific tumor-cell killing with adenovirus vectors containing the Apoptin gene. Gene Therapy 6, 882-892.
25. Rose, M. D., Winston, F., and Hieter, P. (1990). Methods in yeast genetics. A laboratory course manual. Cold Spring Harbor Laboratory Press, Cold Spring Harbor, New York, USA.
26. Sachs, L. and Lotem, J. (1993). Control of programmed cell death in normal and leukemia cells: New implications for therapy. Blood 82, 15-21.

27. Sanger, F., Nicklen, S., and Coulsen, A. R. (1977). DNA sequencing with chain-terminating inhibitors. Proceedings National Academic Sciences USA 74, 5463-5467.
28. Steller, H. (1995). Mechanisms and genes of cellular suicide. Science 267, 1445-1449.
29. Telford, W. G., King, L. E., Fraker, P. J. (1992). Comparative evaluation of several DNA binding dyes in the detection of apoptosis-associated chromatin degradation by flow cytometry. Cytometry 13, 137-143.
30. Teodoro, J. G. and Branton, P. E. (1997). Regulation of apoptosis by viral gene products. Journal of Virology 71, 1739-1746.
31. Thompson, C. B. (1995). Apoptosis in the pathogenesis and treatment of disease. Science 267, 1456-1462.
32. White, E. (1996). Life, death, and the pursuit of apoptosis. Genes and development 10, 1-15.
33. Wyllie, A. H. (1995). The genetic regulation of apoptosis. Current Opinion in Genetics and Development 5, 97-104.
34. Wyllie, A. H., Kerr, J. F. R., Currie, A. R. (1980). Cell death: The significance of apoptosis. International Review of Cytology 68, 251-306.
35. Yang, X., Hubbard, E. J. A., and Carlson, M. (1992). A protein kinase substrate identified by the two-hybrid system. Science 257, 680-682.
36. Zhuang, S. -M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia 9 S1, 118-120.
37. Zhuang, S. -M., Shvarts, A., Van Ormondt, H., Jochemsen, A. -G., Van der Eb, A. J., Noteborn, M. H. M. (1995). Apoptin, a protein derived from chicken anemia virus, induces a p53-independent apoptosis in human osteosarcoma cells. Cancer Research 55, 486-489.
38. Evans G I, Lewis G K, Ramsay G, Bishop J M, (1985), Isolation of monoclonal antibodies specific for human c-myc proto-oncogene product. Mol. Cell. Biol. Dec 5 (12), 3610-3616
39. T. Jenuwein et al. (1998), Cell. Mol. Life Sci. 54, 80-93
40. T. Rozovskaia et al (2000), Oncogene 19, 351-357
41. S. Jacobson and L. Pillus (1999), Curr. Opinion in Gen & Dev. 9, 175-184

---

What is claimed is:

1. An isolated or recombinant nucleic acid sequence encoding an Apoptin-associating proteinaceous substance that localizes in the nucleus of a cell and induces apoptosis, the isolated or recombinant nucleic acid sequence being at least 95% homologous to SEQ ID NO: 10 or SEQ ID NO: 13.

2. The nucleic acid sequence according to claim 1, wherein said Apoptin-associating proteinaceous substance co-localizes with Apoptin.

3. The nucleic acid sequence according to claim 1, wherein said nucleic acid sequence is derived from a cDNA library.

4. The nucleic acid sequence according to claim 3, wherein said cDNA library comprises human cDNA.

5. An isolated host cell comprising a nucleic acid sequence according to claim 1.

6. A vector comprising a nucleic acid sequence according to claim 1.

7. The vector according to claim 6, wherein said vector comprises a gene-delivery vehicle.

8. An isolated host cell comprising a vector according to claim 6 or claim 7.

9. The host cell according to claim 8, wherein said host cell is a eukaryotic cell.

10. The host cell according to claim 9, wherein said host cell is a yeast cell or a vertebrate cell.

11. A composition comprising a nucleic acid sequence that is at least 95% homologous to a nucleic acid sequence of SEQ ID NO: 10 or SEQ ID NO: 13, wherein said composition induces apoptosis.

12. The composition according to claim 11 wherein said apoptosis is p53-independent.

* * * * *

SEQUENCE LISTING

```
<160> NUMBER OF SEQ ID NOS: 15

<210> SEQ ID NO 1
<211> LENGTH: 17
<212> TYPE: DNA
<213> ORGANISM: Artificial Sequence
<220> FEATURE:
<223> OTHER INFORMATION: pACT-primer

<400> SEQUENCE: 1
taccactaca atggatg                                                    17

<210> SEQ ID NO 2
<211> LENGTH: 15
<212> TYPE: PRT
<213> ORGANISM: Artificial Sequence
<220> FEATURE:
<223> OTHER INFORMATION: peptides to generate polyclonal antibodies
<220> FEATURE:
<221> NAME/KEY: SITE
<222> LOCATION: (1)..(15)
<223> OTHER INFORMATION:

<400> SEQUENCE: 2

Glu Glu Ser Thr Pro Val His Asp Ser Pro Gly Lys Asp Asp Ala
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: peptides to generate polyclonal antibodies
<220> FEATURE:
<221> NAME/KEY: SITE
<222> LOCATION: (1)..(15)
<223> OTHER INFORMATION:

<400> SEQUENCE: 3

Asp Ser Phe Lys Thr Lys Asp Ser Phe Arg Thr Ala Lys Ser Lys
 1               5                  10                  15
```

<210> SEQ ID NO 4
<211> LENGTH: 15
<212> TYPE: PRT
<213> ORGANISM: Artificial Sequence
<220> FEATURE:
<223> OTHER INFORMATION: peptides to generate polyclonal antibodies
<220> FEATURE:
<221> NAME/KEY: SITE
<222> LOCATION: (1)..(15)
<223> OTHER INFORMATION:

<400> SEQUENCE: 4

Ile Asp Ile Asp Ile Ser Ser Arg Arg Arg Glu Asp Gln Ser Leu
1               5                   10                  15

<210> SEQ ID NO 5
<211> LENGTH: 29
<212> TYPE: DNA
<213> ORGANISM: Artificial Sequence
<220> FEATURE:
<223> OTHER INFORMATION: primer AAP-4#3F

<400> SEQUENCE: 5
gtcagctcta acactgatgc agataccac                                     29

<210> SEQ ID NO 6
<211> LENGTH: 29
<212> TYPE: DNA
<213> ORGANISM: Artificial Sequence
<220> FEATURE:
<223> OTHER INFORMATION: primer AAP-4#3R

<400> SEQUENCE: 6
gtggtatctg catcagtgtt agagctgac                                     29

<210> SEQ ID NO 7
<211> LENGTH: 28
<212> TYPE: DNA
<213> ORGANISM: Artificial Sequence
<220> FEATURE:
<223> OTHER INFORMATION: primer AAP-4#8F

<400> SEQUENCE: 7
gagagtgact aaatgcacct gggtcagg                                      28

<210> SEQ ID NO 8
<211> LENGTH: 24
<212> TYPE: DNA
<213> ORGANISM: Artificial Sequence
<220> FEATURE:
<223> OTHER INFORMATION: primer AAP-4#9R

<400> SEQUENCE: 8
gttatcccag gtcaagttaa gacc                                          24

<210> SEQ ID NO 9
<211> LENGTH: 10
<212> TYPE: PRT
<213> ORGANISM: Artificial Sequence
<220> FEATURE:
<223> OTHER INFORMATION: Myc-tag
<220> FEATURE:
<221> NAME/KEY: SITE
<222> LOCATION: (1)..(10)
<223> OTHER INFORMATION:

<400> SEQUENCE: 9

```
Glu Gln Lys Leu Ile Ser Glu Asp Leu
1               5               10

<210> SEQ ID NO 10
<211> LENGTH: 770
<212> TYPE: DNA
<213> ORGANISM: Homo sapiens
<220> FEATURE:
<221> NAME/KEY: CDS
<222> LOCATION: (12)..(512)
<223> OTHER INFORMATION:
<220> FEATURE:
<221> NAME/KEY: misc_feature
<223> OTHER INFORMATION: Description of Combined DNA/RNA Molecule:
      sequence of AAP-4

<400> SEQUENCE: 10
gccacgaagg c cgg gag agc tcg ccc tgc acc tac ata act cgg cgg tca      50
             Arg Glu Ser Ser Pro Cys Thr Tyr Ile Thr Arg Arg Ser
              1               5                  10 gtg agg aca aga aca aat ctg aag gag gcc tct gac atc aag ctt gaa      98
Val Arg Thr Arg Thr Asn Leu Lys Glu Ala Ser Asp Ile Lys Leu Glu
    15                  20                  25 cca aat acg ttg aat ggc tat aaa agc agt gtg acg gaa cct tgc ccc     146
Pro Asn Thr Leu Asn Gly Tyr Lys Ser Ser Val Thr Glu Pro Cys Pro
30              35                  40                  45 gac agt ggt gaa cag ctg cag cca gct cct gtg ctg cag gag gaa gaa     194
Asp Ser Gly Glu Gln Leu Gln Pro Ala Pro Val Leu Gln Glu Glu Glu
                50                  55                  60 ctg gct cat gag act gca caa aaa ggg gag gca aag tgt cat aag agt     242
Leu Ala His Glu Thr Ala Gln Lys Gly Glu Ala Lys Cys His Lys Ser
            65                  70                  75 gac aca ggc atg tcc aaa aag aag tca cga caa gga aaa ctt gtg aaa     290
Asp Thr Gly Met Ser Lys Lys Lys Ser Arg Gln Gly Lys Leu Val Lys
        80                  85                  90 cag ttt gca aaa ata gag gaa tct act cca gtg cac gat tct cct gga     338
Gln Phe Ala Lys Ile Glu Glu Ser Thr Pro Val His Asp Ser Pro Gly
    95                  100                 105 aaa gac gac gcg gta cca gat ttg atg ggt ccc cat tct gac cag ggt     386
Lys Asp Asp Ala Val Pro Asp Leu Met Gly Pro His Ser Asp Gln Gly
110                 115                 120                 125 gag cac agt ggc act gtg ggc gtg cct gtg agc tac aca gac tgt gct     434
Glu His Ser Gly Thr Val Gly Val Pro Val Ser Tyr Thr Asp Cys Ala
                130                 135                 140 cct tca ccc gtc ggt tgt tca gtt gtg aca tca gat agc ttc aaa aca     482
Pro Ser Pro Val Gly Cys Ser Val Val Thr Ser Asp Ser Phe Lys Thr
            145                 150                 155 aaa gac agc ttt aga act gca aaa aag taa aaagaagagg cgaatcacaa       532
Lys Asp Ser Phe Arg Thr Ala Lys Lys
            160                 165 ggtatgatgc acagttaatc ctagaaaata actctgggag tcccaaattg actcttcgta   592
ggcgtcatga tagcagcagc aaaacaaatg gaccaagaga atgatgggaa tgaaactctt   652
cccaaaatta agcatcaagt ttaagccaaa gaccatgaca acgataacaa tctcgatgta   712
gcaaagttat aagggtttag ctcaggatta ggaatgtttc acaaaattaa aaaggcat    770

<210> SEQ ID NO 11
<211> LENGTH: 166
<212> TYPE: PRT
<213> ORGANISM: Homo sapiens
<220> FEATURE:
<221> NAME/KEY: misc_feature
<223> OTHER INFORMATION: Description of Combined DNA/RNA Molecule:
```

-continued sequence of AAP-4

<400> SEQUENCE: 11

Arg Glu Ser Ser Pro Cys Thr Tyr Ile Thr Arg Arg Ser Val Arg Thr
1               5                   10                  15

Arg Thr Asn Leu Lys Glu Ala Ser Asp Ile Lys Leu Glu Pro Asn Thr
            20                  25                  30

Leu Asn Gly Tyr Lys Ser Ser Val Thr Glu Pro Cys Pro Asp Ser Gly
        35                  40                  45

Glu Gln Leu Gln Pro Ala Pro Val Leu Gln Glu Glu Leu Ala His
    50                  55                  60

Glu Thr Ala Gln Lys Gly Glu Ala Lys Cys His Lys Ser Asp Thr Gly
65                  70                  75                  80

Met Ser Lys Lys Lys Ser Arg Gln Gly Lys Leu Val Lys Gln Phe Ala
                85                  90                  95

Lys Ile Glu Glu Ser Thr Pro Val His Asp Ser Pro Gly Lys Asp Asp
            100                 105                 110

Ala Val Pro Asp Leu Met Gly Pro His Ser Asp Gln Gly Glu His Ser
        115                 120                 125

Gly Thr Val Gly Val Pro Val Ser Tyr Thr Asp Cys Ala Pro Ser Pro
    130                 135                 140

Val Gly Cys Ser Val Val Thr Ser Asp Ser Phe Lys Thr Lys Asp Ser
145                 150                 155                 160

Phe Arg Thr Ala Lys Lys
                165

<210> SEQ ID NO 12
<211> LENGTH: 256
<212> TYPE: PRT
<213> ORGANISM: Homo sapiens
<220> FEATURE:
<221> NAME/KEY: SITE
<222> LOCATION: (1)..(256)
<223> OTHER INFORMATION: /note="Amino-acid sequence of the analyse
      region of the Apoptin-associating clone AAP-4, wherein X is a
      stopcodon"
<220> FEATURE:
<221> NAME/KEY: misc_feature
<222> LOCATION: (170)..(247)
<223> OTHER INFORMATION: Xaa can be any amino acid

<400> SEQUENCE: 12

His Glu Gly Arg Glu Ser Ser Pro Cys Thr Tyr Ile Thr Arg Arg Ser
1               5                   10                  15

Val Arg Thr Arg Thr Asn Leu Lys Glu Ala Ser Asp Ile Lys Leu Glu
            20                  25                  30

Pro Asn Thr Leu Asn Gly Tyr Lys Ser Ser Val Thr Glu Pro Cys Pro
        35                  40                  45

Asp Ser Gly Glu Gln Leu Gln Pro Ala Pro Val Leu Gln Glu Glu
    50                  55                  60

Leu Ala His Glu Thr Ala Gln Lys Gly Glu Ala Lys Cys His Lys Ser
65                  70                  75                  80

Asp Thr Gly Met Ser Lys Lys Lys Ser Arg Gln Gly Lys Leu Val Lys
                85                  90                  95

Gln Phe Ala Lys Ile Glu Glu Ser Thr Pro Val His Asp Ser Pro Gly
            100                 105                 110

Lys Asp Asp Ala Val Pro Asp Leu Met Gly Pro His Ser Asp Gln Gly
        115                 120                 125

```
Glu His Ser Gly Thr Val Gly Val Pro Val Ser Tyr Thr Asp Cys Ala
    130                 135                 140
Pro Ser Pro Val Gly Cys Ser Val Val Thr Ser Asp Ser Phe Lys Thr
145                 150                 155                 160
Lys Asp Ser Phe Arg Thr Ala Lys Lys Xaa Lys Glu Glu Ala Asn His
                165                 170                 175
Lys Val Xaa Cys Thr Val Asn Pro Arg Lys Xaa Leu Trp Glu Ser Gln
            180                 185                 190
Ile Asp Ser Ser Xaa Ala Ser Xaa Xaa Gln Gln Gln Asn Lys Trp Thr
                195                 200                 205
Lys Arg Met Met Gly Met Lys Leu Phe Pro Lys Leu Ser Ile Lys Phe
    210                 215                 220
Lys Pro Lys Thr Met Thr Thr Ile Thr Ile Ser Met Xaa Gln Ser Tyr
225                 230                 235                 240
Lys Gly Leu Ala Gln Asp Xaa Glu Cys Phe Thr Lys Leu Lys Arg His
                245                 250                 255

<210> SEQ ID NO 13
<211> LENGTH: 5690
<212> TYPE: DNA
<213> ORGANISM: Homo sapiens
<220> FEATURE:
<221> NAME/KEY: CDS
<222> LOCATION: (236)..(2866)
<223> OTHER INFORMATION:

<400> SEQUENCE: 13 cggcaggca  gcggggcgat  gaggtgagga  cgcccgggaa  ccggaggcgg  caccgcgcgg      60
cgcacggacc  tgggacgcgg  agtcctgaag  ccggcggacg  gttttcgtac  gggcggccgt     120
gcgcgaggcg  aggagagaac  attgaaagta  ttctctaagc  tatttgaaga  gagtgactaa     180
atgcacctgg  gtcaggctgt  ctgtgggtat  gaagtggttg  ggagaatcca  agaac atg     238
                                                                  Met
                                                                    1 gtg gtg aat ggc agg aga aat gga ggc aag ttg tct aat gac cat cag        286
Val Val Asn Gly Arg Arg Asn Gly Gly Lys Leu Ser Asn Asp His Gln
        5                   10                  15 cag aat caa tca aaa tta cag cac acg ggg aag gac acc ctg aag gct        334
Gln Asn Gln Ser Lys Leu Gln His Thr Gly Lys Asp Thr Leu Lys Ala
    20                  25                  30 ggc aaa aat gca gtc gag agg agg tcg aac aga tgt aat ggt aac tcg        382
Gly Lys Asn Ala Val Glu Arg Arg Ser Asn Arg Cys Asn Gly Asn Ser
35                  40                  45 gga ttt gaa gga cag agt cgc tat gta cca tcc tct gga atg tcc gcc        430
Gly Phe Glu Gly Gln Ser Arg Tyr Val Pro Ser Ser Gly Met Ser Ala
50                  55                  60                  65 aag gaa ctc tgt gaa aat gat gac cta gca acc agt ttg gtt ctt gat        478
Lys Glu Leu Cys Glu Asn Asp Asp Leu Ala Thr Ser Leu Val Leu Asp
                70                  75                  80 ccc tat tta ggt ttt caa aca cac aaa atg aat act agc gcc ttt cct        526
Pro Tyr Leu Gly Phe Gln Thr His Lys Met Asn Thr Ser Ala Phe Pro
            85                  90                  95 tcg agg agc tca agg cat ttt tca aaa tct gac agt ttt tct cac aac        574
Ser Arg Ser Ser Arg His Phe Ser Lys Ser Asp Ser Phe Ser His Asn
        100                 105                 110 aac cct gtg aga ttt agg cct att aaa gga agg cag gaa gaa cta aag        622
Asn Pro Val Arg Phe Arg Pro Ile Lys Gly Arg Gln Glu Glu Leu Lys
    115                 120                 125 gaa gta att gaa cgt ttt aag aaa gat gaa cac ttg gag aaa gcc ttc        670
```

-continued

| | | |
|---|---|---|
| Glu Val Ile Glu Arg Phe Lys Lys Asp Glu His Leu Glu Lys Ala Phe<br>130               135                      140                       145 | | |
| aaa tgt ttg act tca ggc gaa tgg gca cgg cac tat ttt ctc aac aag<br>Lys Cys Leu Thr Ser Gly Glu Trp Ala Arg His Tyr Phe Leu Asn Lys<br>                         150                     155                     160 | 718 | |
| aat aaa atg cag gag aaa tta ttc aaa gaa cat gta ttt att tat ttg<br>Asn Lys Met Gln Glu Lys Leu Phe Lys Glu His Val Phe Ile Tyr Leu<br>             165                     170                     175 | 766 | |
| cga atg ttt gca act gac agt gga ttt gaa ata ttg cca tgt aat aga<br>Arg Met Phe Ala Thr Asp Ser Gly Phe Glu Ile Leu Pro Cys Asn Arg<br>    180                     185                     190 | 814 | |
| tac tca tca gaa caa aat gga gcc aaa ata gtt gca aca aaa gag tgg<br>Tyr Ser Ser Glu Gln Asn Gly Ala Lys Ile Val Ala Thr Lys Glu Trp<br>195                       200                     205 | 862 | |
| aaa cga aat gac aaa ata gaa tta ctg gtg ggt tgt att gcc gaa ctt<br>Lys Arg Asn Asp Lys Ile Glu Leu Leu Val Gly Cys Ile Ala Glu Leu<br>210                       215                     220                     225 | 910 | |
| tca gaa att gag gag aac atg cta ctt aga cat gga gaa aac gac ttc<br>Ser Glu Ile Glu Glu Asn Met Leu Leu Arg His Gly Glu Asn Asp Phe<br>                       230                     235                     240 | 958 | |
| agt gtc atg tac tcc aca agg aaa aac tgt gct caa ctc tgg ctg ggt<br>Ser Val Met Tyr Ser Thr Arg Lys Asn Cys Ala Gln Leu Trp Leu Gly<br>             245                     250                     255 | 1006 | |
| cct gct gcg ttt ata aac cat gat tgc aga cct aat tgt aag ttt gtg<br>Pro Ala Ala Phe Ile Asn His Asp Cys Arg Pro Asn Cys Lys Phe Val<br>        260                     265                     270 | 1054 | |
| tca act ggt cga gat aca gca tgt gtg aag gct cta aga gac att gaa<br>Ser Thr Gly Arg Asp Thr Ala Cys Val Lys Ala Leu Arg Asp Ile Glu<br>275                       280                     285 | 1102 | |
| cct gga gaa gaa att tct tgt tat tat gga gat ggg ttc ttt gga gaa<br>Pro Gly Glu Glu Ile Ser Cys Tyr Tyr Gly Asp Gly Phe Phe Gly Glu<br>290                       295                     300                     305 | 1150 | |
| aat aat gag ttc tgc gag tgt tac act tgc gaa aga cgg ggc act ggt<br>Asn Asn Glu Phe Cys Glu Cys Tyr Thr Cys Glu Arg Arg Gly Thr Gly<br>                       310                     315                     320 | 1198 | |
| gct ttt aaa tcc aga gtg gga ctg cct gcg cct gct cct gtt atc aat<br>Ala Phe Lys Ser Arg Val Gly Leu Pro Ala Pro Ala Pro Val Ile Asn<br>             325                     330                     335 | 1246 | |
| agc aaa tat gga ctc aga gaa aca gat aaa cgt tta aat agg ctt aaa<br>Ser Lys Tyr Gly Leu Arg Glu Thr Asp Lys Arg Leu Asn Arg Leu Lys<br>        340                     345                     350 | 1294 | |
| aag tta ggt gac agc agc aaa aat tca gac agt caa tct gtc agc tct<br>Lys Leu Gly Asp Ser Ser Lys Asn Ser Asp Ser Gln Ser Val Ser Ser<br>355                       360                     365 | 1342 | |
| aac act gat gca gat acc act cag gaa aaa aac aat gca act tct aac<br>Asn Thr Asp Ala Asp Thr Thr Gln Glu Lys Asn Asn Ala Thr Ser Asn<br>370                       375                     380                     385 | 1390 | |
| cga aaa tct tca gtt ggc gta aaa aag aat agc aag agc aga acg tta<br>Arg Lys Ser Ser Val Gly Val Lys Lys Asn Ser Lys Ser Arg Thr Leu<br>                       390                     395                     400 | 1438 | |
| acg agg caa tct atg tca aga att cca gct tct tcc aac tct acc tca<br>Thr Arg Gln Ser Met Ser Arg Ile Pro Ala Ser Ser Asn Ser Thr Ser<br>             405                     410                     415 | 1486 | |
| tct aag cta act cat ata aat aat tcc agg gta cca aag aaa ctg aag<br>Ser Lys Leu Thr His Ile Asn Asn Ser Arg Val Pro Lys Lys Leu Lys<br>        420                     425                     430 | 1534 | |
| aag cct gca aag cct tta ctt tca aag ata aaa ttg aga aat cat tgc<br>Lys Pro Ala Lys Pro Leu Leu Ser Lys Ile Lys Leu Arg Asn His Cys<br>435                       440                     445 | 1582 | |

```
aag cgg ctg gag caa aag aat gct tca aga aaa ctc gaa atg gga aac    1630
Lys Arg Leu Glu Gln Lys Asn Ala Ser Arg Lys Leu Glu Met Gly Asn
450             455                 460                 465 tta gta ctg aaa gag cct aaa gta gtt ctg tat aaa aat ttg ccc att    1678
Leu Val Leu Lys Glu Pro Lys Val Val Leu Tyr Lys Asn Leu Pro Ile
                470                 475                 480 aaa aaa gat aag gag cca gag gga cca gcc caa gcc gca gtt gcc agc    1726
Lys Lys Asp Lys Glu Pro Glu Gly Pro Ala Gln Ala Ala Val Ala Ser
            485                 490                 495 ggg tgc ttg act aga cac gcg gcg aga gaa cac aga cag aat cct gtg    1774
Gly Cys Leu Thr Arg His Ala Ala Arg Glu His Arg Gln Asn Pro Val
        500                 505                 510 aga ggt gct cat tcg cag ggg gag agc tcg ccc tgc acc tac ata act    1822
Arg Gly Ala His Ser Gln Gly Glu Ser Ser Pro Cys Thr Tyr Ile Thr
    515                 520                 525 cgg cgg tca gtg agg aca aga aca aat ctg aag gag gcc tct gac atc    1870
Arg Arg Ser Val Arg Thr Arg Thr Asn Leu Lys Glu Ala Ser Asp Ile
530                 535                 540                 545 aag ctt gaa cca aat acg ttg aat ggc tat aaa agc agt gtg acg gaa    1918
Lys Leu Glu Pro Asn Thr Leu Asn Gly Tyr Lys Ser Ser Val Thr Glu
                550                 555                 560 cct tgc ccc gac agt ggt gaa cag ctg cag cca gct cct gtg ctg cag    1966
Pro Cys Pro Asp Ser Gly Glu Gln Leu Gln Pro Ala Pro Val Leu Gln
            565                 570                 575 gag gaa gaa ctg gct cat gag act gca caa aaa ggg gag gca aag tgt    2014
Glu Glu Glu Leu Ala His Glu Thr Ala Gln Lys Gly Glu Ala Lys Cys
        580                 585                 590 cat aag agt gac aca ggc atg tcc aaa aag aag tca cga caa gga aaa    2062
His Lys Ser Asp Thr Gly Met Ser Lys Lys Lys Ser Arg Gln Gly Lys
    595                 600                 605 ctt gtg aaa cag ttt gca aaa ata gag gaa tct act cca gtg cac gat    2110
Leu Val Lys Gln Phe Ala Lys Ile Glu Glu Ser Thr Pro Val His Asp
610                 615                 620                 625 tct cct gga aaa gac gac gcg gta cca gat ttg atg ggt ccc cat tct    2158
Ser Pro Gly Lys Asp Asp Ala Val Pro Asp Leu Met Gly Pro His Ser
                630                 635                 640 gac cag ggt gag cac agt ggc act gtg ggc gtg cct gtg agc tac aca    2206
Asp Gln Gly Glu His Ser Gly Thr Val Gly Val Pro Val Ser Tyr Thr
            645                 650                 655 gac tgt gct cct tca ccc gtc ggt tgt tca gtt gtg aca tca gat agc    2254
Asp Cys Ala Pro Ser Pro Val Gly Cys Ser Val Val Thr Ser Asp Ser
        660                 665                 670 ttc aaa aca aaa gac agc ttt aga act gca aaa agt aaa aag aag agg    2302
Phe Lys Thr Lys Asp Ser Phe Arg Thr Ala Lys Ser Lys Lys Lys Arg
    675                 680                 685 cga atc aca agg tat gat gca cag tta atc cta gaa aat aac tct ggg    2350
Arg Ile Thr Arg Tyr Asp Ala Gln Leu Ile Leu Glu Asn Asn Ser Gly
690                 695                 700                 705 att ccc aaa ttg act ctt cgt agg cgt cat gat agc agc agc aaa aca    2398
Ile Pro Lys Leu Thr Leu Arg Arg Arg His Asp Ser Ser Ser Lys Thr
                710                 715                 720 aat gac caa gag aat gat gga atg aac tct tcc aaa ata agc atc aag    2446
Asn Asp Gln Glu Asn Asp Gly Met Asn Ser Ser Lys Ile Ser Ile Lys
            725                 730                 735 tta agc aaa gac cat gac aac gat aac aat ctc tat gta gca aag ctt    2494
Leu Ser Lys Asp His Asp Asn Asp Asn Asn Leu Tyr Val Ala Lys Leu
        740                 745                 750 aat aat gga ttt aac tca gga tca ggc agt agt tct aca aaa tta aaa    2542
Asn Asn Gly Phe Asn Ser Gly Ser Gly Ser Ser Ser Thr Lys Leu Lys
    755                 760                 765
```

```
atc cag cta aaa cga gat gag gaa aat agg ggg tct tat aca gag ggg       2590
Ile Gln Leu Lys Arg Asp Glu Glu Asn Arg Gly Ser Tyr Thr Glu Gly
770             775                 780                 785 ctt cat gaa aat ggg gtg tgc tgc agt gat cct ctt tct ctc ttg gag       2638
Leu His Glu Asn Gly Val Cys Cys Ser Asp Pro Leu Ser Leu Leu Glu
                790                 795                 800 tct cga atg gag gtg gat gac tat agt cag tat gag gaa gaa agt aca       2686
Ser Arg Met Glu Val Asp Asp Tyr Ser Gln Tyr Glu Glu Glu Ser Thr
            805                 810                 815 gat gat tcc tcc tct tct gag ggc gat gaa gag gag gat gac tat gat       2734
Asp Asp Ser Ser Ser Ser Glu Gly Asp Glu Glu Glu Asp Asp Tyr Asp
        820                 825                 830 gat gac ttt gaa gac gat ttt att cct ctt cct cca gct aag cgc ttg       2782
Asp Asp Phe Glu Asp Asp Phe Ile Pro Leu Pro Pro Ala Lys Arg Leu
    835                 840                 845 agg tta ata gtt gga aaa gac tct ata gat att gac att tct tca agg       2830
Arg Leu Ile Val Gly Lys Asp Ser Ile Asp Ile Asp Ile Ser Ser Arg
850                 855                 860                 865 aga aga gaa gat cag tct tta agg ctt aat gcc taa gctcttggtc            2876
Arg Arg Glu Asp Gln Ser Leu Arg Leu Asn Ala
                870                 875 ttaacttgac ctgggataac tactttaaag aaataaaaaa ttccagtcaa ttattcctca     2936
actgaaagtt tagtggcagc acttctattg tcccttcact tatcagcata ctattgtaga    2996
aagtgtacag catactgact caattcttaa gtctgatttg tgcaaatttt tatcgtactt    3056
tttaaatagc cttcttacgt gcaattctga gttagaggta aagccctgtt gtaaaataaa    3116
ggctcaagca aaattgtaca gtgatagcaa cttttccacac aggacgttga aaacagtaat   3176
gtggctacac agtttttta actgtaagag catcagctgg ctctttaata tatgactaaa     3236
caataattta aaacaaatca tagtagcagc atattaaggg tttctagtat gctaatatca    3296
ccagcaatga tctttggctt tttgatttat ttgctagatg tttccccctt ggagttttgt    3356
cagtttcaca ctgtttgctg gcccaggtgt actgtttgtg gcctttgtta atatcgcaaa    3416
ccattggttg ggagtcagat tggtttctta aaaaaaaaa aaaaatgaca tacgtgacag     3476 ctcactttc agttcattat atgtacgagg gtagcagtgt gtgggatgag gttcgataca     3536
gcgtatttat tgcttgtcat gtaaattaaa aaccttgtat ttaactcttt tcaatccttt    3596
tagataaaat tgttctttgc aagaatgatt ggtgcttatt ttttcaaaaa tttgctgtga    3656
acaacgtgat gacaacaagc aacatttatc taatgaacta cagctatctt aatttggttc    3716
ttcaagtttt ctgttgcact tgtaaaatgc tacaaggaat attaaaaaaa tctattcact    3776
ttaacttata atagtttatg aaataaaaac atgagtcaca gcttttgttc tgtggtaacc    3836
tataaaaaaa gtttgtcttt gagattcaat gtaaagaact gaaaacaatg tatatgttgt    3896
aaatatttgt gtgttgtgag acatttttgt cataagaaat taaagaact taccaggaag     3956 gttttaagt ttagaaatat tcatgccaat aaaataggaa attataaata tatagttta      4016 agcactgcat cagtgggagt tcttggctta tgttagttta tgttagttta ttatgaaaac    4076
atcaaagatt tttttgacta tattatcagt taaacaaaaa ggagtcagat ttaatttgtt    4136
ttttgaagca ctttgagaaa ttaattttaa ttaacttaat gagcaaattt ttattactac    4196
tttatgttca ataccaggtt cttttcattt ctctggatta ttttgcaaat cattggacag    4256
agaatttggg aatataaatc tgtaacaggt gttgacacca gtaggtctct ttatttctgg    4316
gaaatgtgta cctgtacttt ctgatataca gtgttcctaa gtaaaaatca attcagggga    4376
```

```
tttgtatagt gtctatagga aagtagccca tgtcttgaaa tatgaaaagg aatctgaagg  4436
tcatgaaaag tccagtggag aaaatctcaa tgcttactgt tactactaat tgattcctac  4496
tagtttccag gtttgggggg atattgtttc aatgacgctc cttaagactg ttgattgccc  4556
ataggttcca aatagaaatt aagactcatg aacatttta gaaagtagat tgttttctcc  4616
tggttctcta aggaactact tctgcagtct tacatagtct catccttgtt tgttgtggtg  4676
cagtcgaact cctcaggcgt ttggaaagca tgtggtagac cttcttccac acccacccat  4736
accccccgttc actgcgtctg gaggtcttca acagtgaagt agggcagccc acacagcctc  4796
tcaggagcac ctgtccgagg cacccggagc actttgcaga gcacgtccag ccctcatggg  4856
gtccctgcat agaaatgtga accccctgcca ctgaggaaga tgaaggtaga ccctgtgtct  4916
ggaggtgctg gagggcagcg ggtcacctct tgtattccca ccttagtttg gggtgttttg  4976
aagaggttca gagactaaat cttaaacctt atttgaatac caacgatagc tattttggga  5036
atttcgatct taaaaagtga caaaacacat ttcccatttt cattttcag ctgaatttta  5096
gtaacttatt tttgatgttt taattttatc atggcctcct ctttggaggc caaccttccc  5156
atgggtctca aagcagtgac atttggtagt aaatcactgc ctctcaggag tcggtatgca  5216
caagcactca gcagccactg ttgatgcctt ctagggaaac ctaatttccg ttggtaaagg  5276
taggggcctc ggaactgttc cggatctgct gtagaacttc accgtgtgga atggtgacag  5336
ccacacaccg ttgaccagtt tagaagaggt tgcattcaat aaaactctta gcttgagctt  5396
atgcaatgat tggttaagat tttggcattg taagaattag gagatgatca tagaaatata  5456
tgtaaagtat tcaattttca atcattttca aattactgtt ataaattgtt tttgctgagt  5516
tgtaatactt ttgagataca atgtattcct tgtactgaaa gaatgaaaaa ggactttttc  5576
agcatttgag gtaagttctt taacgtttca ttaaaaacat tttttacaaa tattttgtac  5636
atgcacttgc agtattgagg ttaatcattt taataaattc ggaaattaaa aaaa          5690
```

<210> SEQ ID NO 14
<211> LENGTH: 876
<212> TYPE: PRT
<213> ORGANISM: Homo sapiens

<400> SEQUENCE: 14

```
Met Val Val Asn Gly Arg Arg Asn Gly Gly Lys Leu Ser Asn Asp His
1               5                   10                  15

Gln Gln Asn Gln Ser Lys Leu Gln His Thr Gly Lys Asp Thr Leu Lys
            20                  25                  30

Ala Gly Lys Asn Ala Val Glu Arg Arg Ser Asn Arg Cys Asn Gly Asn
        35                  40                  45

Ser Gly Phe Glu Gly Gln Ser Arg Tyr Val Pro Ser Ser Gly Met Ser
    50                  55                  60

Ala Lys Glu Leu Cys Glu Asn Asp Asp Leu Ala Thr Ser Leu Val Leu
65                  70                  75                  80

Asp Pro Tyr Leu Gly Phe Gln Thr His Lys Met Asn Thr Ser Ala Phe
                85                  90                  95

Pro Ser Arg Ser Ser Arg His Phe Ser Lys Ser Asp Ser Phe Ser His
            100                 105                 110

Asn Asn Pro Val Arg Phe Arg Pro Ile Lys Gly Arg Gln Glu Glu Leu
        115                 120                 125

Lys Glu Val Ile Glu Arg Phe Lys Lys Asp Glu His Leu Glu Lys Ala
    130                 135                 140
```

-continued

```
Phe Lys Cys Leu Thr Ser Gly Glu Trp Ala Arg His Tyr Phe Leu Asn
145                 150                 155                 160

Lys Asn Lys Met Gln Glu Lys Leu Phe Lys Glu His Val Phe Ile Tyr
                165                 170                 175

Leu Arg Met Phe Ala Thr Asp Ser Gly Phe Glu Ile Leu Pro Cys Asn
            180                 185                 190

Arg Tyr Ser Ser Glu Gln Asn Gly Ala Lys Ile Val Ala Thr Lys Glu
        195                 200                 205

Trp Lys Arg Asn Asp Lys Ile Glu Leu Leu Val Gly Cys Ile Ala Glu
    210                 215                 220

Leu Ser Glu Ile Glu Glu Asn Met Leu Leu Arg His Gly Glu Asn Asp
225                 230                 235                 240

Phe Ser Val Met Tyr Ser Thr Arg Lys Asn Cys Ala Gln Leu Trp Leu
                245                 250                 255

Gly Pro Ala Ala Phe Ile Asn His Asp Cys Arg Pro Asn Cys Lys Phe
            260                 265                 270

Val Ser Thr Gly Arg Asp Thr Ala Cys Val Lys Ala Leu Arg Asp Ile
        275                 280                 285

Glu Pro Gly Glu Glu Ile Ser Cys Tyr Tyr Gly Asp Gly Phe Phe Gly
    290                 295                 300

Glu Asn Asn Glu Phe Cys Glu Cys Tyr Thr Cys Glu Arg Arg Gly Thr
305                 310                 315                 320

Gly Ala Phe Lys Ser Arg Val Gly Leu Pro Ala Pro Ala Pro Val Ile
                325                 330                 335

Asn Ser Lys Tyr Gly Leu Arg Glu Thr Asp Lys Arg Leu Asn Arg Leu
            340                 345                 350

Lys Lys Leu Gly Asp Ser Ser Lys Asn Ser Asp Ser Gln Ser Val Ser
        355                 360                 365

Ser Asn Thr Asp Ala Asp Thr Thr Gln Glu Lys Asn Asn Ala Thr Ser
    370                 375                 380

Asn Arg Lys Ser Ser Val Gly Val Lys Lys Asn Ser Lys Ser Arg Thr
385                 390                 395                 400

Leu Thr Arg Gln Ser Met Ser Arg Ile Pro Ala Ser Ser Asn Ser Thr
                405                 410                 415

Ser Ser Lys Leu Thr His Ile Asn Asn Ser Arg Val Pro Lys Lys Leu
            420                 425                 430

Lys Lys Pro Ala Lys Pro Leu Leu Ser Lys Ile Lys Leu Arg Asn His
        435                 440                 445

Cys Lys Arg Leu Glu Gln Lys Asn Ala Ser Arg Lys Leu Glu Met Gly
    450                 455                 460

Asn Leu Val Leu Lys Glu Pro Lys Val Val Leu Tyr Lys Asn Leu Pro
465                 470                 475                 480

Ile Lys Lys Asp Lys Glu Pro Glu Gly Pro Ala Gln Ala Ala Val Ala
                485                 490                 495

Ser Gly Cys Leu Thr Arg His Ala Ala Arg Glu His Arg Gln Asn Pro
            500                 505                 510

Val Arg Gly Ala His Ser Gln Gly Glu Ser Ser Pro Cys Thr Tyr Ile
        515                 520                 525

Thr Arg Arg Ser Val Arg Thr Arg Thr Asn Leu Lys Glu Ala Ser Asp
    530                 535                 540

Ile Lys Leu Glu Pro Asn Thr Leu Asn Gly Tyr Lys Ser Ser Val Thr
545                 550                 555                 560

Glu Pro Cys Pro Asp Ser Gly Glu Gln Leu Gln Pro Ala Pro Val Leu
```

```
                565                 570                 575
Gln Glu Glu Glu Leu Ala His Glu Thr Ala Gln Lys Gly Glu Ala Lys
            580                 585                 590
Cys His Lys Ser Asp Thr Gly Met Ser Lys Lys Ser Arg Gln Gly
            595                 600             605
Lys Leu Val Lys Gln Phe Ala Lys Ile Glu Ser Thr Pro Val His
        610                 615                 620
Asp Ser Pro Gly Lys Asp Ala Val Pro Asp Leu Met Gly Pro His
625                 630                 635                 640
Ser Asp Gln Gly Glu His Ser Gly Thr Val Gly Val Pro Val Ser Tyr
            645                 650                 655
Thr Asp Cys Ala Pro Ser Pro Val Gly Cys Ser Val Val Thr Ser Asp
            660                 665                 670
Ser Phe Lys Thr Lys Asp Ser Phe Arg Thr Ala Lys Ser Lys Lys Lys
            675                 680                 685
Arg Arg Ile Thr Arg Tyr Asp Ala Gln Leu Ile Leu Glu Asn Asn Ser
        690                 695                 700
Gly Ile Pro Lys Leu Thr Leu Arg Arg His Asp Ser Ser Lys
705                 710                 715                 720
Thr Asn Asp Gln Glu Asn Asp Gly Met Asn Ser Ser Lys Ile Ser Ile
            725                 730                 735
Lys Leu Ser Lys Asp His Asp Asn Asn Leu Tyr Val Ala Lys
            740                 745                 750
Leu Asn Asn Gly Phe Asn Ser Gly Ser Gly Ser Ser Thr Lys Leu
            755                 760                 765
Lys Ile Gln Leu Lys Arg Asp Glu Asn Arg Gly Ser Tyr Thr Glu
        770                 775                 780
Gly Leu His Glu Asn Gly Val Cys Cys Ser Asp Pro Leu Ser Leu Leu
785                 790                 795                 800
Glu Ser Arg Met Glu Val Asp Asp Tyr Ser Gln Tyr Glu Glu Ser
            805                 810                 815
Thr Asp Ser Ser Ser Ser Glu Gly Asp Glu Glu Asp Asp Tyr
            820                 825                 830
Asp Asp Asp Phe Glu Asp Asp Phe Ile Pro Leu Pro Pro Ala Lys Arg
            835                 840                 845
Leu Arg Leu Ile Val Gly Lys Asp Ser Ile Asp Ile Asp Ile Ser Ser
        850                 855                 860
Arg Arg Arg Glu Asp Gln Ser Leu Arg Leu Asn Ala
865                 870                 875

<210> SEQ ID NO 15
<211> LENGTH: 120
<212> TYPE: PRT
<213> ORGANISM: Homo Sapiens
<220> FEATURE:
<221> NAME/KEY: SITE
<222> LOCATION: (1)..(120)
<223> OTHER INFORMATION: /note="SET domain of the AAP-4 protein,
      location 185-304"

<400> SEQUENCE: 15

Gly Phe Glu Ile Leu Pro Cys Asn Arg Tyr Ser Ser Glu Gln Asn Gly
1               5                   10                  15

Ala Lys Ile Val Ala Thr Lys Glu Trp Lys Arg Asn Asp Lys Ile Glu
            20                  25                  30

Leu Leu Val Gly Cys Ile Ala Glu Leu Ser Glu Ile Glu Glu Asn Met
```

-continued

```
                35                  40                  45
Leu Leu Arg His Gly Glu Asn Asp Phe Ser Val Met Tyr Ser Thr Arg
    50                  55                  60

Lys Asn Cys Ala Gln Leu Trp Leu Gly Pro Ala Ala Phe Ile Asn His
65                  70                  75                  80

Asp Cys Arg Pro Asn Cys Lys Phe Val Ser Thr Gly Arg Asp Thr Ala
                85                  90                  95

Cys Val Lys Ala Leu Arg Asp Ile Glu Pro Gly Glu Glu Ile Ser Cys
                100                 105                 110

Tyr Tyr Gly Asp Gly Phe Phe Gly
                115                 120
```